(12) United States Patent
Tsuruoka et al.

(10) Patent No.: US 11,035,853 B2
(45) Date of Patent: Jun. 15, 2021

(54) HEALTH MONITORING SYSTEM, HEALTH MONITORING METHOD, AND HEALTH MONITORING PROGRAM

(71) Applicant: SYMAX INC., Tokyo (JP)

(72) Inventors: Maria Tsuruoka, Tokyo (JP); Kentaro Goto, Tokyo (JP)

(73) Assignee: SYMAX, Inc., Tokyo (JP)

(*) Notice: Subject to any disclaimer, the term of this patent is extended or adjusted under 35 U.S.C. 154(b) by 246 days.

(21) Appl. No.: 16/342,883

(22) PCT Filed: Oct. 17, 2016

(86) PCT No.: PCT/JP2016/080750
§ 371 (c)(1),
(2) Date: Apr. 17, 2019

(87) PCT Pub. No.: WO2018/073877
PCT Pub. Date: Apr. 26, 2018

(65) Prior Publication Data
US 2019/0293636 A1 Sep. 26, 2019

(51) Int. Cl.
*G01N 33/52* (2006.01)
*G16H 10/40* (2018.01)
(Continued)

(52) U.S. Cl.
CPC ............ *G01N 33/52* (2013.01); *G01N 33/50* (2013.01); *G01N 35/00584* (2013.01); *G01N 35/10* (2013.01); *G16H 10/40* (2018.01)

(58) Field of Classification Search
CPC .. G16H 10/40; G01N 35/10; G01N 35/00584; G01N 33/50; G01N 33/52
See application file for complete search history.

(56) References Cited

U.S. PATENT DOCUMENTS

2018/0108440 A1* 4/2018 Stevens ............... G16H 50/20
2019/0062813 A1* 2/2019 Amin .................. B01L 3/508
(Continued)

FOREIGN PATENT DOCUMENTS

| JP | 4-113268 | 4/1992 |
| JP | 8-5631 | 1/1996 |

(Continued)

OTHER PUBLICATIONS

International Search Report completed Jan. 24, 2017 in PCT/JP2016/080750 filed Oct. 17, 2016.
(Continued)

*Primary Examiner* — Shogo Sasaki
(74) *Attorney, Agent, or Firm* — Levine Bagade Han LLP

(57) ABSTRACT

In a health monitoring system analyzing urination of a user using a toilet, a transfer unit that immerses a film producing a color reaction for a composition to be detected in reserved water containing urine includes a clamping unit that clamps the film in an opening/closing part of an upper clamping member and a lower clamping member of which one ends are connected through a connection shaft, an upper drive unit that drives an upper rod to which the upper clamping member is connected in a longitudinal direction of the upper rod, a lower drive unit that drives a lower rod to which the lower clamping member is connected in a longitudinal direction of the lower rod, and a moving drive unit that drives a first moving rod connected to the upper clamping member and a second moving rod connected to the lower clamping member in longitudinal directions of the first and second moving rods.

11 Claims, 12 Drawing Sheets

(51) Int. Cl.
  *G01N 35/00* (2006.01)
  *G01N 35/10* (2006.01)
  *G01N 33/50* (2006.01)

(56) References Cited

U.S. PATENT DOCUMENTS

| | | | |
|---|---|---|---|
| 2019/0293636 A1* | 9/2019 | Tsuruoka | G01N 35/10 |
| 2020/0167631 A1* | 5/2020 | Rezgui | G06F 8/30 |
| 2020/0187863 A1* | 6/2020 | Tu | A61B 5/207 |
| 2020/0289000 A1* | 9/2020 | Hall | A61B 5/02125 |
| 2020/0395112 A1* | 12/2020 | Ronner | G16H 10/60 |

FOREIGN PATENT DOCUMENTS

| | | |
|---|---|---|
| JP | 2004-279219 | 10/2004 |
| JP | 2006-266078 | 10/2006 |
| JP | 2013-036817 | 2/2013 |
| JP | 2013-090748 | 5/2013 |

OTHER PUBLICATIONS

Microfilm of the specification and drawings annexed to the request of Japanese Utility Model Application No. 99203/1989 (Laid-open No. 39154/1991) (Toto Ltd.), Apr. 16, 1991.
Microfilm of the specification and drawings annexed to the request of Japanese Utility Model Application No. 99201/1989 (Laid-open No. 39152/1991) (Toto Ltd.), Apr. 16, 1991.

* cited by examiner

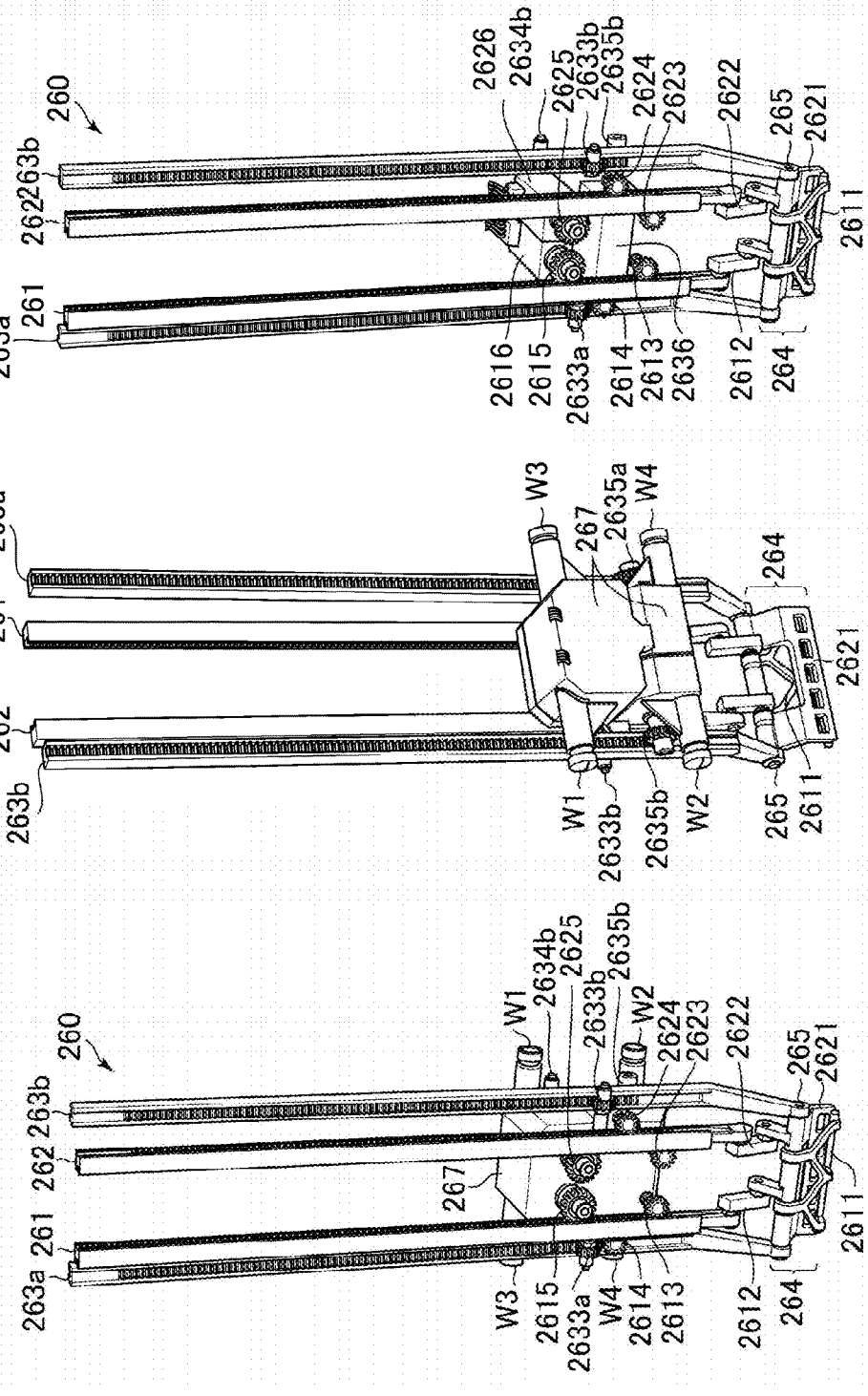

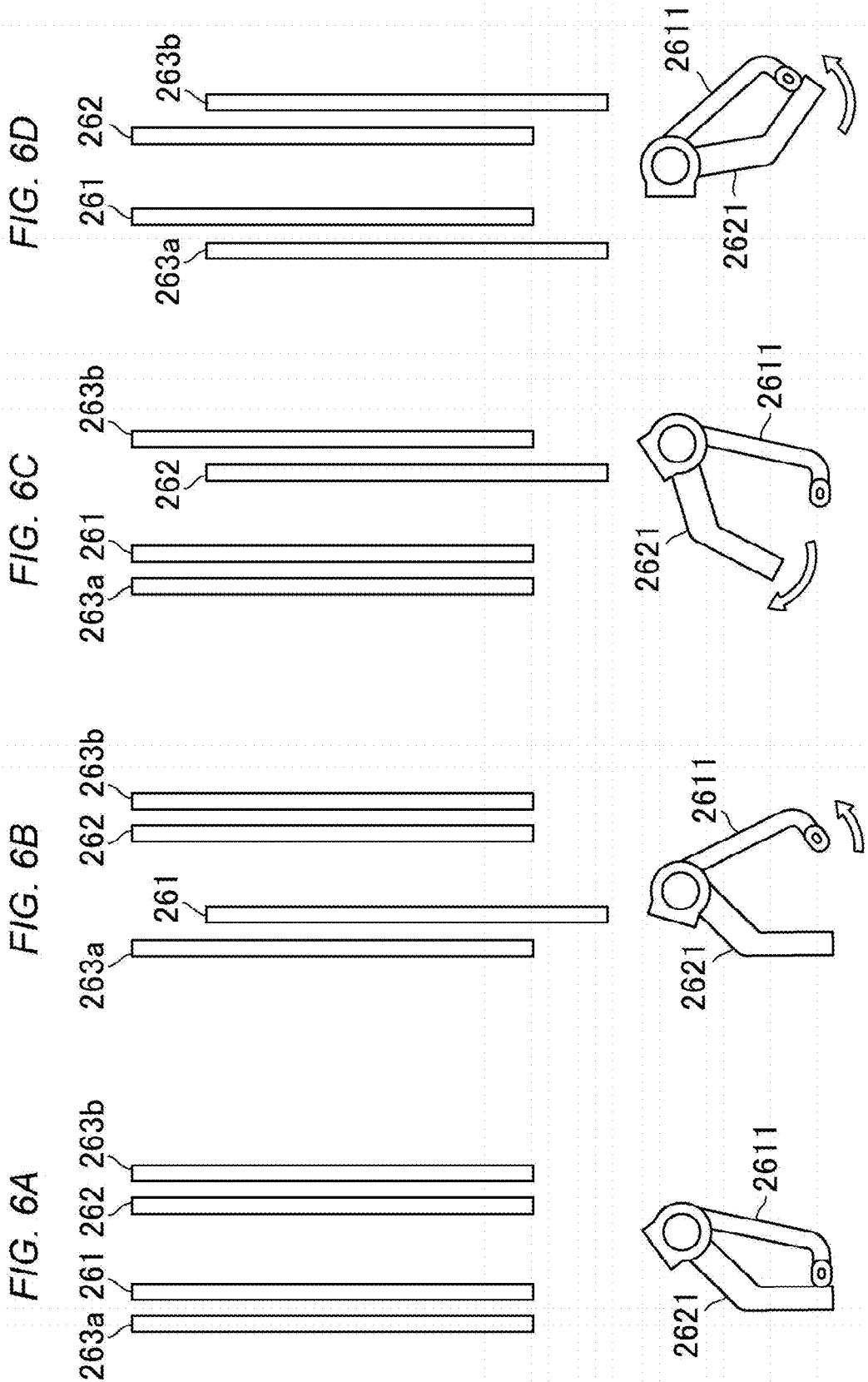

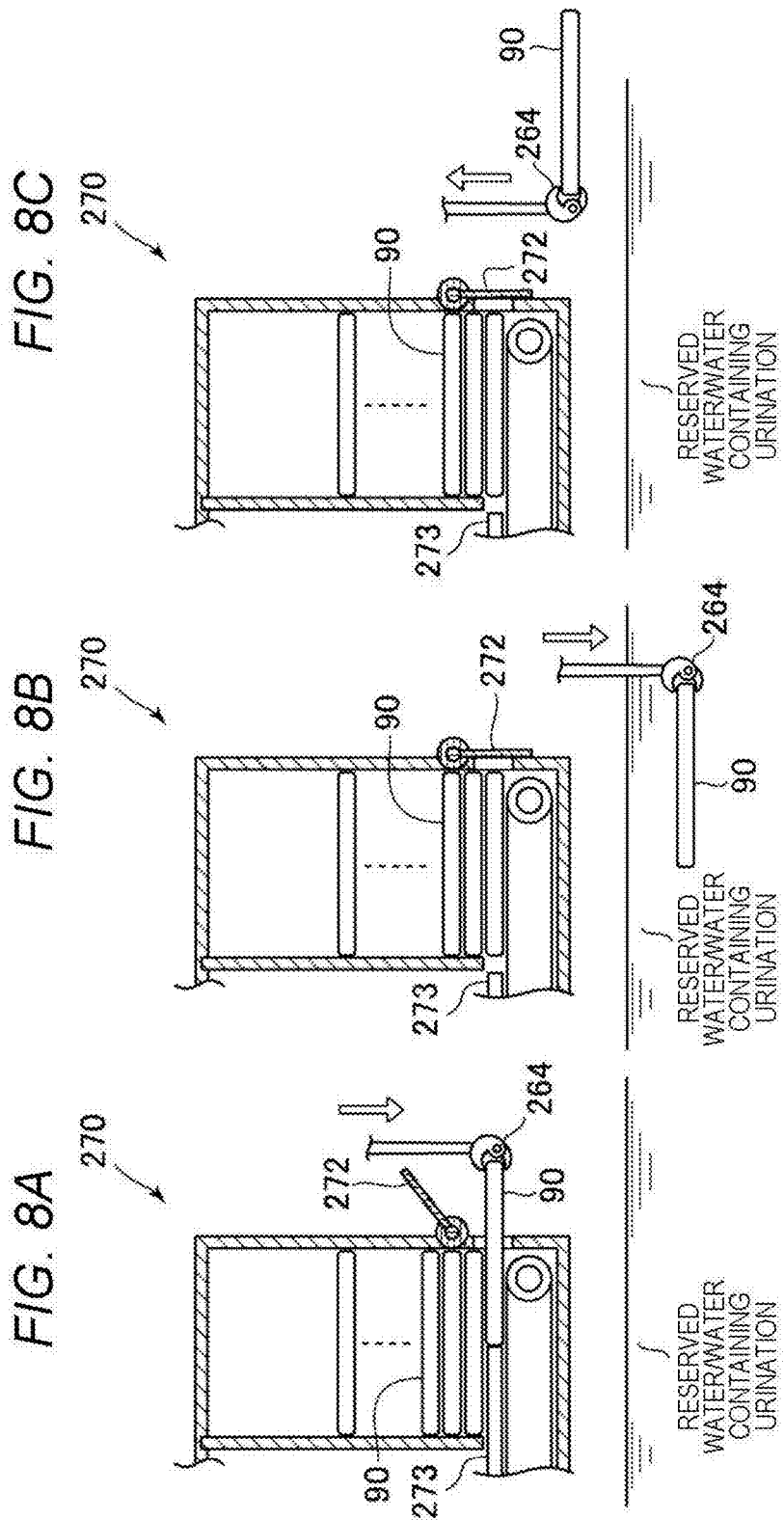

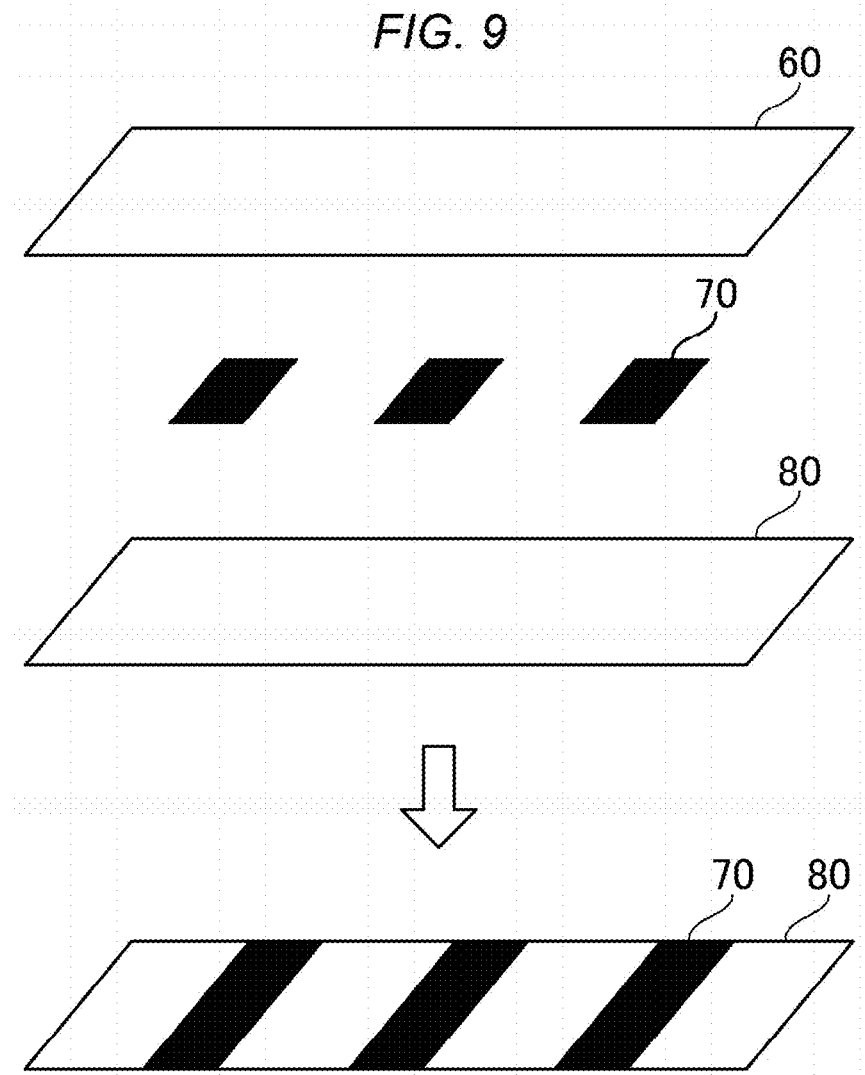

FIG. 10

| TOILET INFORMATION DB | THRESHOLD DB | MEASUREMENT/INSPECTION RESULT DB | DICTIONARY DATA DB | USER DB |
|---|---|---|---|---|
| TOILET ID | MEASUREMENT ITEM | USER ID | MEASURED VALUE | USER ID |
| TOILET MODEL NUMBER | THRESHOLD FOR EACH MEASUREMENT ITEM (ABSOLUTE) | MEASUREMENT ITEM | CHARACTERISTIC VECTOR | NAME |
| WATER AMOUNT | THRESHOLD FOR EACH MEASUREMENT ITEM (FOR EACH USER) | MEASURED VALUE | INSPECTION RESULT (ANALYSIS RESULT, PREDICTION RESULT) | SEX |
| WATER TEMPERATURE | | INSPECTION ITEM | | HEIGHT |
| PRESENCE/ABSENCE OF DETERGENT | | INSPECTION RESULT (ANALYSIS RESULT, PREDICTION RESULT) | | WEIGHT |
| FACILITY INFORMATION (LATITUDE/LONGITUDE INFORMATION, ADDRESS, AND BUILDING) | | MEASUREMENT DATE AND TIME (YEAR/MONTH/DATE, HOUR/MINUTE/SECOND) | | MASS INFORMATION |
| USE START TIME (YEAR/MONTH/DATE) | | INSPECTION DATE AND TIME (YEAR/MONTH/DATE, HOUR/MINUTE/SECOND) | | ASSOCIATED TOILET ID |

FIG. 11

| INFORMATION ON MEASUREMENT AND ANALYSIS RESULTS | INFORMATION ON ESTIMATED DISEASE OR THE LIKE | MEASUREMENT AND ANALYSIS RESULT INFORMATION | INFORMATION ON ESTIMATED DISEASE OR THE LIKE |
|---|---|---|---|
| URINE SUGAR LEVEL | DIABETES MELLITUS | KETONE | DIABETES, DIARRHEA, VOMITING, EXCESSIVE DIET/AFTER INTENSE EXERCISE, HYPEREMESIS |
| | ENDOCRINE DISORDERS (HYPERTHYROIDISM, ACROMEGALY, OR THE LIKE) | NITRITE | URINARY TRACT INFECTION (CYSTITIS OR THE LIKE) |
| | ACUTE AND CHRONIC PANCREATITIS AND CUSHING'S SYNDROME | WHITE BLOOD CELL | URINARY TRACT INFECTION (CYSTITIS OR THE LIKE) |
| | KIDNEY DISEASE (CHRONIC RENAL FAILURE, INTERSTITIAL NEPHRITIS, OR THE LIKE)/PHECHROMOCYTOMA/MYOCARDIAL INFARCTION/CEREBROVASCULAR DISEASE/AFTER GASTRECTOMY | | ALLERGIC DISEASE |
| URINE PROTEIN VALUE | PRERENAL<br>· MULTIPLE MYELOMA, HEMOLYTIC ANEMIA, COLLAGEN DISEASE, AND HEART FAILURE | | URINARY STONE |
| | RENAL<br>· ACUTE AND CHRONIC NEPHRITIS, NEPHROTIC SYNDROME, AMYLOID KIDNEY, CADMIUM POISONING, AND VITAMIN D POISONING | CREATININE | RENAL DYSFUNCTION (INCLUDING MILD RENAL DYSFUNCTION) |
| | POSTRENAL<br>· CYSTITIS, PROSTATITIS, TUMOR (BLADDER, PROSTATE, OR THE LIKE), CALCULUS (BLADDER, URETER, OR THE LIKE) | ALBUMIN (INCLUDING MICROALBUMIN) | DIABETES, DIABETIC NEPHROPATHY (INCLUDING EARLY NEPHROPATHY) |
| URINARY OCCULT BLOOD | KIDNEY DISEASE<br>· ACUTE AND CHRONIC NEPHRITIS (GLOMERULONEPHRITIS, LUPUS NEPHRITIS OR THE LIKE), KIDNEY STONES, KIDNEY TUMOR, FLOATING KIDNEY, RENAL TRAUMA AND CYSTIC KIDNEY | | FOLLOWING SIGN<br>· PERSISTENT PROTEINURIA, PROLIFERATIVE RETINOPATHY, AND CARDIOVASCULAR DISEASE |
| | URETERAL DISEASES<br>· URETER STONES AND URETER TRACT TUMOR | SPECIFIC GRAVITY | GREAT VALUE (HIGH-SPECIFIC GRAVITY)<br>· DIABETES MELLITUS<br>· DEHYDRATION (VOMITING, DIARRHEA, SWEATING, FEVER, OR THE LIKE)<br>· AFTER USING CONTRAST MEDIUM<br>· AFTER EXERCISE OR THE LIKE · SMALL VALUE (LOW SPECIFIC GRAVITY)<br>· DIABETES INSIPIDUS<br>· NEPHRITIS<br>· RENAL FAILURE OR THE LIKE |
| | BLADDER DISEASE<br>· CYSTITIS, BLADDER STONE, AND BLADDER TUMOR | TURBIDITY | DEHYDRATION SYMPTOM OR THE LIKE |
| | OTHER UROLOGICAL DISEASES<br>· PROSTATITIS, PROSTATE CANCER, AND URETHRITIS | UA (URIC ACID) | FOLLOWING DISEASE TYPE CLASSIFICATION<br>· URIC ACID PRODUCTION EXCESS TYPE, URIC ACID EXCRETION REDUCTION TYPE, AND MIXED TYPE |
| | DISEASES OTHER THAN UROLOGY TRACT<br>· LEUKEMIA, HEMOLYTIC ANEMIA (PAROXYSMAL NOCTURNAL HEMOGLOBINURIA OR THE LIKE), MYOCARDIAL INFARCTION, MUSCULAR DYSTROPHY, MUSCLE INJURY, SEVERE BURN, PAROXYSMAL NOCTURNAL HEMOGLOBINURIA | LUTEINIZING HORMONE | OVULATION |
| pH VALUE | ACIDIC URINE<br>· DIABETES, GOUT, NEPHRITIS, FEVER, DEHYDRATION, DIARRHEA | LUTEIN HORMONE | PREGNANCY |
| | ALKALINE URINE<br>· VOMITING, URINARY TRACT INFECTION, HYPERVENTILATION | | |
| UROBILINOGEN | LIVER DISEASE (HEPATITIS, CIRRHOSIS OR THE LIKE) | | |
| | HEMOLYTIC ANEMIA (PAROXYSMAL NOCTURNAL HEMOGLOBINURIA OR THE LIKE), MEGALOBLASTIC ANEMIA, HEART FAILURE, BOWEL OBSTRUCTION, EXCESSIVE CONSTIPATION | | |

HEALTH MONITORING SYSTEM, HEALTH MONITORING METHOD, AND HEALTH MONITORING PROGRAM

CROSS-REFERENCE TO RELATED APPLICATIONS

This application is a U.S. national application filed under 35 U.S.C. 371 to PCT International Application No. PCT/JP2016/080750 filed Oct. 17, 2016, the content of which is incorporated herein by reference in its entirety.

BACKGROUND OF THE INVENTION

Field of the Invention

The present invention relates to a health monitoring system, a health monitoring method, and a health monitoring program, and more particularly, to a health monitoring system, a health monitoring method, and a health monitoring program being installed in a toilet, analyzing urination, and predicting a likelihood of having a disease.

Description of Related Art

In accordance with an increase in health consciousness in recent years, conventionally, there are many services that monitor a health state by analyzing the state of urine (the amount or the compositions) and gives advice. In a case in which there is an abnormality in a body, the state of urine may easily change, and, in order to check an abnormality in the body, it is effective to regularly monitor the state of urine.

As such a urine analyzing technology, for example, in Patent Document 1, a urination information measuring device that stores data representing a correlation between the concentration of a specific composition contained in urine of one instance of urination of a person, which is actually measured, and the concentration of the specific composition contained in all of the urine of one day, which is actually measured, the concentration of the specific composition contained in all of the urine of one day of a person to be measured is acquired through conversion using the correlation and calculates the concentration of excretion of the specific composition in the whole one-day urine of the person to be measured on the basis of the acquired concentration has been disclosed.

In addition, in Patent Document 2, a urination information measuring device that calculates the amount of urination and a urination flow rate by using a bowl of a toilet accumulating urine and a urine data measuring means that measures a volume and a weight of urine accumulated in the bowl has been disclosed. The urination measuring device disclosed in Patent Document 2 calculates the amount of urination and a urine flow rate on the basis of each water level or a water level change rate at the time of starting urination or at the time of ending urination and calculates urination information by performing a process using a particle filter by applying a predetermined vibration model to the calculated data.

PATENT DOCUMENTS

[Patent Document 1]
Japanese Unexamined Patent Application Publication No. 2013-36817

[Patent Document 2]
Japanese Unexamined Patent Application Publication No. 2013-90748

SUMMARY OF THE INVENTION

However, according to the invention described in Patent Document 1, the device is largely configured as a casing and a sensor unit, and it is necessary to pour urine excreted by a person to be measured over the sensor unit with the casing gripped by the hand of the person to be measured or the like, and the usability is not necessarily sufficient.

In addition, according to the invention described in Patent Document 2, in a case in which water level data of reserved water inside the bowl or measurement of sewage pressure of a sewer pipe is used as a means for measuring the volume or the weight of urine accumulated in the bowl of the toilet, elements configuring the toilet are used, and accordingly, it cannot be applied to a toilet that has already been installed. Accordingly, in the urination information measuring device described in Patent Document 2, the versatility is insufficient, and the usability is not necessarily sufficient.

Thus, an object of the present invention is to provide a health monitoring system, a health monitoring method, and a health monitoring program that are simple and conveniently used in an analysis of urination such as a urine composition analysis or the like and a prediction of a likelihood of having a disease based on a result of the analysis.

According to one aspect of the present invention, there is provided a health monitoring system analyzing urination of a user using a toilet, the health monitoring system including a storage unit that stores a film producing a color reaction for a composition to be detected, a transfer unit that immerses the film taken out of the storage unit in reserved water of the toilet into which the urination has flown, an imaging unit that generates imaging information by imaging the film after being immersed in the reserved water, an analysis unit that analyzes urine compositions of the urination on the basis of the imaging information, and a prediction unit that predicts a likelihood of having a disease on the basis of a result of the analysis using the analysis unit, wherein the transfer unit includes a clamping unit that clamps the film in an opening/closing part of an upper clamping member and a lower clamping member of which one ends are connected through a connection shaft, an upper drive unit that drives an upper rod to which the upper clamping member is connected in a longitudinal direction of the upper rod, a lower drive unit that drives a lower rod to which the lower clamping member is connected in a longitudinal direction of the lower rod, and a moving drive unit that drives a first moving rod connected to the upper clamping member through the connection shaft and a second moving rod connected to the lower clamping member through the connection shaft in longitudinal directions of the first moving rod and the second moving rod, wherein the upper rod, the lower rod, the first moving rod, and the second moving rod are positioned approximately in parallel with each other in a longitudinal direction, the opening/closing part of the clamping unit is opened or closed by changing a relative position of at least one of the upper rod and the lower rod in the longitudinal direction with respect to the first moving rod and the second moving rod, and a position of the clamping unit is changed by moving the first moving rod, the second moving rod, the upper rod, and the lower rod in the longitudinal direction without changing relative positions of the upper rod and the lower rod with respect to the first moving rod and the second moving rod.

In addition, in the health monitoring system according to one aspect of the present invention, the transfer unit rotates the clamping unit using the connection shaft as its rotation shaft by changing the relative positions of the upper rod and the lower rod in the longitudinal direction with respect to the first moving rod and the second moving rod.

In addition, in the health monitoring system according to one aspect of the present invention, in a case in which the film clamped by the clamping unit is immersed into the reserved water, a housing unit is arranged at a position, which is separate from the clamping unit by a predetermined length, in the transfer unit.

In addition, in the health monitoring system according to one aspect of the present invention, the transfer unit is arranged at a position at which the film can be taken out of the storage unit, and the film clamped by the clamping unit can be imaged by the imaging unit.

In addition, the health monitoring system according to one aspect of the present invention further includes an illuminance sensor unit that measures illuminance of the toilet, and the analysis unit corrects the imaging information on the basis of illuminance information relating to illumination of the toilet and analyzes urine compositions of the urination on the basis of the corrected imaging information.

In addition, in the health monitoring system according to one aspect of the present invention, the storage unit stores the films to be stacked and includes an opening part, an extrusion part that extrudes the film from the opening part, a lid part that closes the opening part, and a drive unit that drives the extrusion part and the lid part, wherein, when the film is extruded by the extrusion part, the drive unit drives the lid part such that the opening part is open.

In addition, in the health monitoring system according to one aspect of the present invention, the storage unit stores the films to be stacked and includes an opening part and an extrusion part that extrudes the film from the opening part, and a dehumidification mechanism that includes at least one of a dehumidifier and a dehumidification module is further stored in the storage unit together with the films.

In addition, the health monitoring system according to one aspect of the present invention further includes a measurement unit that measures fluid information relating to a fluid in reserved water into which urination of a user using the toilet has flown; an acquisition unit that acquires shape information of a bowl of the toilet, water amount information of reserved water, and environment information relating to a surrounding environment of the measurement unit; and an interpretation unit that analyzes the urination by analyzing a fluid model acquired by modeling a fluid on the basis of at least one of the fluid information measured by the measurement unit, the shape information, the water amount information, and the environment information, wherein the analysis unit corrects the imaging information on the basis of urination information acquired as a result of an analysis using the interpretation unit and the fluid information and analyzes urine compositions of the urination on the basis of the corrected imaging information.

In addition, in the health monitoring system according to one aspect of the present invention, the prediction unit generates a characteristic vector from the imaging information, identifies the generated characteristic vector using training data, and predicts a likelihood of having a disease on the basis of the identified characteristic vector.

Furthermore, according to one aspect of the present invention, there is provided a health monitoring method for analyzing urination of a user using a toilet, the health monitoring method including a storage step of storing a film producing a color reaction for a composition to be detected in a storage unit, a transfer step of causing a transfer unit to immerse the film taken out of the storage unit in reserved water of the toilet into which the urination has flown using a transfer unit, an imaging step of generating imaging information by imaging the film after being immersed in the reserved water, an analysis step of analyzing urine compositions of the urination on the basis of the imaging information, and a prediction step of predicting a likelihood of having a disease on the basis of a result of the analysis in the analysis step, wherein the transfer unit includes a clamping unit that clamps the film in an opening/closing part of an upper clamping member and a lower clamping member of which one ends are connected through a connection shaft, an upper drive unit that drives an upper rod to which the upper clamping member is connected in a longitudinal direction of the upper rod, a lower drive unit that drives a lower rod to which the lower clamping member is connected in a longitudinal direction of the lower rod, a moving drive unit that drives a first moving rod connected to the upper clamping member through the connection shaft and a second moving rod connected to the lower clamping member through the connection shaft in longitudinal directions of the first moving rod and the second moving rod, and a housing unit that houses the moving drive unit, the upper drive unit, and the lower drive unit, wherein the upper rod, the lower rod, the first moving rod, and the second moving rod are positioned approximately in parallel with each other in a longitudinal direction, and in the transfer step, the opening/closing part of the clamping unit is opened or closed by changing a relative position of at least one of the upper rod and the lower rod in the longitudinal direction with respect to the first moving rod and the second moving rod, and a position of the clamping unit is changed by moving the first moving rod, the second moving rod, the upper rod, and the lower rod in the longitudinal direction without changing relative positions of the upper rod and the lower rod with respect to the first moving rod and the second moving rod.

According to one aspect of the present invention, there is provided a program controlling a health monitoring system analyzing urination of a user using a toilet, the program causing a computer to realize: a transfer function of causing a transfer unit to take a film out of a storage unit storing films producing a color reaction for a composition to be detected and to immerse the film into reserved water of the toilet into which the urination has flown, an imaging function of generating imaging information by imaging the film after being immersed in the reserved water, an analysis function of analyzing urine compositions of the urination on the basis of the imaging information, and a prediction function of predicting a likelihood of having a disease on the basis of a result of the analysis using the analysis function, wherein the transfer unit includes a clamping unit that clamps the film in an opening/closing part of an upper clamping member and a lower clamping member of which one ends are connected through a connection shaft; an upper drive unit that drives an upper rod to which the upper clamping member is connected in a longitudinal direction of the upper rod, a lower drive unit that drives a lower rod to which the lower clamping member is connected in a longitudinal direction of the lower rod, a moving drive unit that drives a first moving rod connected to the upper clamping member through the connection shaft and a second moving rod connected to the lower clamping member through the connection shaft in longitudinal directions of the first moving rod and the second moving rod, and a housing unit that houses the moving drive unit, the upper drive unit, and the lower drive unit, wherein the upper rod, the lower rod, the first moving rod, and the second moving rod are positioned approximately in parallel with each other in a longitudinal direction, and the computer causes the transfer unit to open or close the opening/closing part of the clamping unit by changing a relative position of at least one of the upper rod and the lower rod in the longitudinal direction with respect to the first moving rod and the second moving rod and to change a position of the clamping unit by moving the first moving rod, the second moving rod, the upper rod, and the lower rod in the longitudinal direction without changing relative positions of the upper rod and the lower rod with respect to the first moving rod and the second moving rod.

According to one aspect of the present invention, a person to be measured can measure urine compositions by excreting in a toilet as usual, and accordingly, the urine compositions can be measured more simply and sanitarily than in a measurement performed by pouring urine over a device, whereby the usability can be improved.

In addition, in one aspect of the present invention, the amount of urine is analyzed by analyzing the movement of a fluid through a fluid simulation, and accordingly, a degree at which urine is diluted by reserved water can be taken into account, and an analysis with a high accuracy can be performed.

According to one aspect of the present invention, simplicity and usability in an analysis of urination information and a prediction of a likelihood of having a disease can be improved.

BRIEF DESCRIPTION OF THE DRAWINGS

FIG. 4A is a schematic diagram of a transfer unit according to one aspect of the present invention in a front-side perspective view.

FIG. 4B is a schematic diagram of a transfer unit according to one aspect of the present invention in a rear-side perspective view.

FIG. 4C is a schematic diagram of an internal structure of a transfer unit according to one aspect of the present invention.

FIG. 6A is a schematic diagram illustrating a positional relation between opening/closing of the clamping unit and each rod in a transfer unit according to one aspect of the present invention.

FIG. 6B is a schematic diagram illustrating a positional relation between opening/closing of the clamping unit and each rod in a transfer unit according to one aspect of the present invention.

FIG. 6C is a schematic diagram illustrating a positional relation between opening/closing of the clamping unit and each rod in a transfer unit according to one aspect of the present invention.

FIG. 6D is a schematic diagram illustrating a positional relation between opening/closing of the clamping unit and each rod in a transfer unit according to one aspect of the present invention.

FIG. 8A is a diagram schematically illustrating operations of a transfer unit and a storage unit according to one aspect of the present invention.

FIG. 8B is a diagram schematically illustrating operations of a transfer unit and a storage unit according to one aspect of the present invention.

FIG. 8C is a diagram schematically illustrating operations of a transfer unit and a storage unit according to one aspect of the present invention.

FIG. 9 is a diagram schematically illustrating the configuration of a film according to one aspect of the present invention.

FIG. 10 is a diagram illustrating an example of the configuration of a database (DB) used in a health monitoring system according to one aspect of the present invention.

FIG. 11 is a diagram illustrating one example of a DB representing association between a result of measurement/analysis and information such as a disease and the like used in a health monitoring system according to one aspect of the present invention.

DETAILED DESCRIPTION OF THE INVENTION

Hereinafter, an embodiment of the present invention will be described with reference to the drawings.

Figure 1:
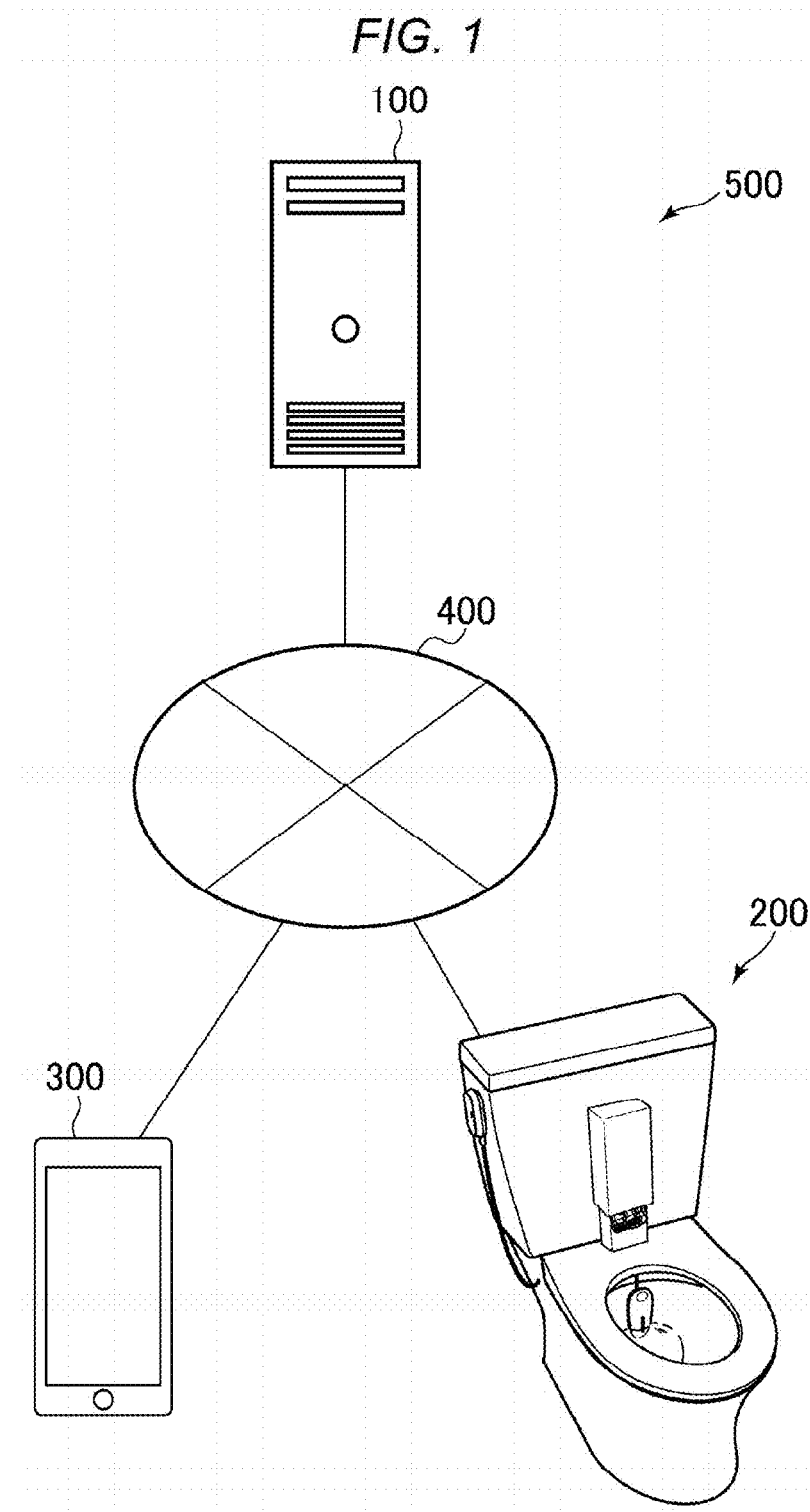
FIG. 1 is a diagram illustrating one example of the configuration of a health monitoring system according to one aspect of the present invention.

First, an overview of a health monitoring system will be described. FIG. 1 is a diagram illustrating one example of the configuration of a health monitoring system according to one embodiment of the present invention. As illustrated in FIG. 1, the health monitoring system 500 is a health monitoring system that analyzes urination of a user using a toilet and includes a server 100, a measurement device 200 mainly installed in the toilet, and a user terminal 300. The server 100 is connected to the measurement device 200 and the user terminal 300 through a network 400. Although only one server 100, one measurement device 200, and one user terminal 300 are illustrated in FIG. 1 for simplifying description, it is apparent that there may be more servers, measurement devices, and user terminals. In addition, a specific device of the user terminal 300 is not limited to a smartphone as illustrated in the drawing and, for example, may be a mobile terminal, a tablet terminal, a personal computer, or any other electronic device.

Although details will be described later, as illustrated in FIG. 1, the health monitoring system 500 analyzes compositions of urine by installing the measurement device 200 in a toilet or the like that has already been installed and immersing a film, which produces a color reaction with a composition to be detected, in the urination (for example, a bioassay method). In addition, a user's disease is predicted on the basis of an analysis result. In addition, the measurement device 200 measures fluid information relating to a fluid in reserved water in which urination of a user using a toilet flows, and the server 100 analyzes urination by analyzing a fluid model acquired by modeling an area in which a fluid flows on the basis of the measured fluid information, whereby an accuracy of a result of the analysis using the film can be improved on the basis of the urination information of the analyzed urination. In addition, the "fluid information" represents information required for a fluid analysis and is composed of shape information relating to the shape of a bowl of a toilet, water amount information, water temperature information, and environment information of reserved water inside the bowl of the toilet and water (hereinafter, referred to as "urination-containing water") including urine of a user using the toilet in the reserved water, and the like. Here, the "environment information" represents information relating to environments of the toilet such as a detergent, and a composition and the like contained in the reserved water. In addition, the "urination information" represents various kinds of information relating to urination of a user and is composed to include the amount of urine, a urine temperature, a urine composition, and the like. Here, the measurement device 200 may be installed by post-installation in a toilet that has already been installed as in the drawing or may be disposed as an integrated type in the form of being built in a toilet in advance.

Figure 2:
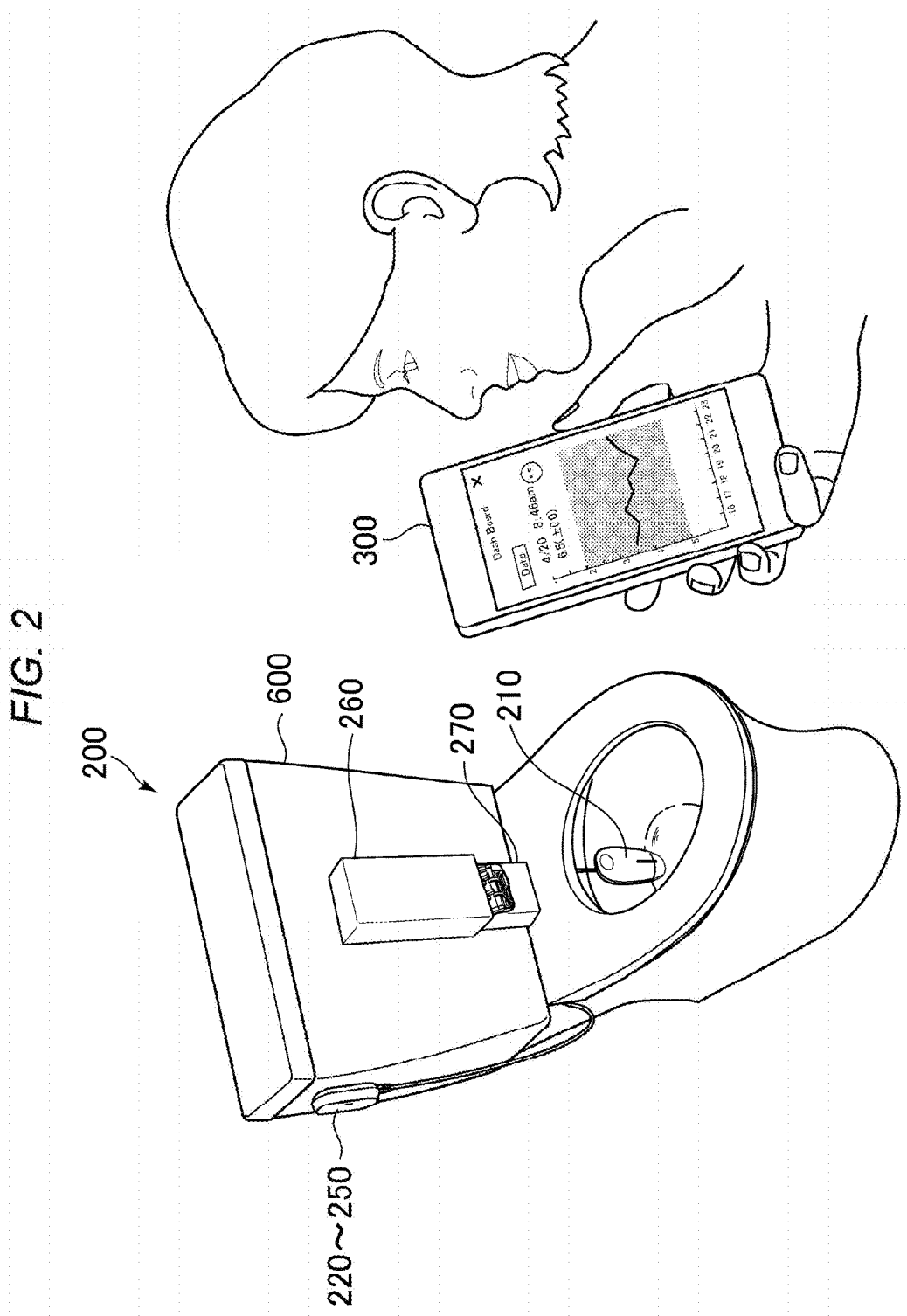
FIG. 2 is a schematic diagram illustrating an example of use of a health monitoring system according to one aspect of the present invention.

FIG. 2 is a schematic diagram illustrating an example of use of a health monitoring system according to one aspect of the present invention. In the example illustrated in FIG. 2, although a case in which the measurement device 200 is installed in a western-type toilet 600 is illustrated, the type of toilet is not limited to the western-style toilet, and any type of toilet such as a Japanese-style toilet or the like may be used as long as there is reserved water for flushing and draining in the toilet. In addition, reference signs of the measurement device 200 will be described later with reference to FIG. 3. The user terminal 300 has a mobile application, which is provided by the health monitoring system 500 according to one embodiment of the present invention (hereinafter, referred to as a "health monitoring application"), mounted therein. In accordance with the health monitoring application, a result of monitoring of a health state as illustrated in FIG. 2 (including the result of an analysis of urination and the result of a prediction; details thereof will be described later) is displayed in the user terminal 300, and accordingly, a user can check his or her health state.

As illustrated in FIGS. 1 and 2, the health monitoring system 500 according to one aspect of the present invention can be realized in a simplified manner by installing the measurement device 200 in a toilet or the like. Accordingly, for example, a user can determine a disease or a sign of a disease by only performing an ordinary urination action while being in his or her own house or office, and accordingly, a health monitoring service that is simple and easy to use and has high sustainability can be provided. In addition, the health monitoring system 500 is not limited to applications at a house or an office and can be also used in a nursing facility or a hospital for health management of patients, and risk reduction on the operation side of the facility can be achieved. An overview of the health monitoring system 500 has been described as above.

Figure 3:
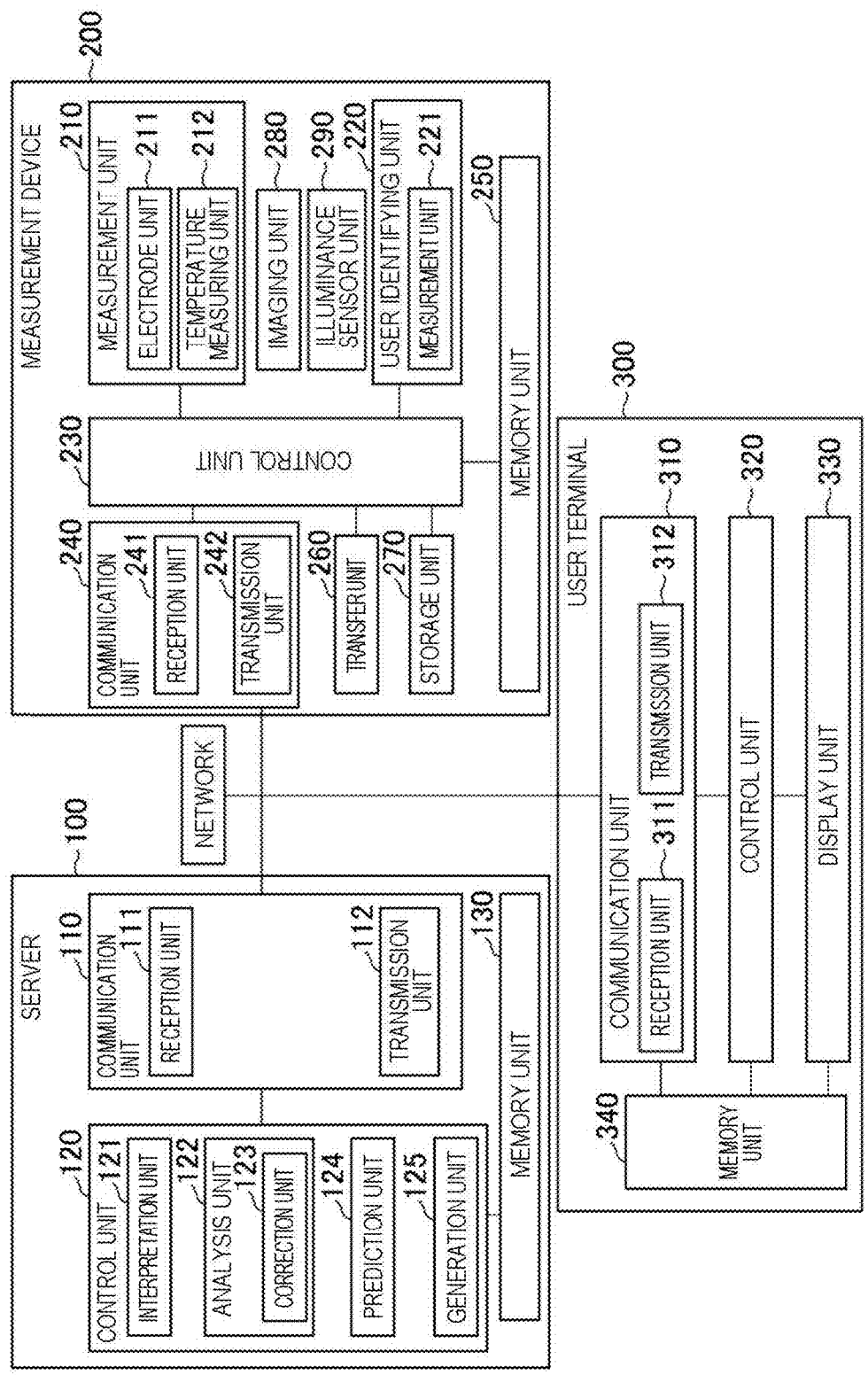
FIG. 3 is a block diagram illustrating one example of a health monitoring system according to one aspect of the present invention.

FIG. 3 is a block diagram illustrating one example of a health monitoring system according to one embodiment of the present invention. As illustrated in the drawing, the health monitoring system 500 according to one embodiment of the present invention includes a server 100, a measurement device 200, and a user terminal 300. In addition, although examples using a cloud computing form have been illustrated in FIGS. 1 and 3, the present invention is not limited thereto, and, for example, the health monitoring system 500 may be composed of only the single measurement device 200 or only the measurement device 200 and the user terminal 300. In other words, the arrangement of each unit may be appropriately changed among the server 100, the measurement device 200, and the user terminal 300 in accordance with an operation environment of each device, a situation, and the like. For example, an interpretation unit 121, an analysis unit 122, a prediction unit 124, and a generation unit 125 of the server 100 may be disposed in a control unit 230 of the measurement device 200 or in a control unit 320 of the user terminal 300.

While details will be described later, the function of each unit will be briefly described. First, the measurement device 200 will be described. As illustrated in FIG. 3, the measurement device 200 is configured to include a measurement unit 210, a user identifying unit 220, a control unit 230, a communication unit 240, a memory unit 250, a transfer unit 260, a storage unit 270, an imaging unit 280, and an illuminance sensor unit 290.

In addition, respective units of the measurement device 200 may be disposed in a plurality of devices. For example, as illustrated in FIG. 2, the measurement unit 210 may be disposed inside a measurement target, and the user identifying unit 220, the control unit 230, the communication unit 240, and the memory unit 250 may be disposed together in another device. In addition, the storage unit 270 that stores films used for an analysis of urine and the transfer unit 260 that clamps and moves a film may be disposed at places that don't disturb a user using the toilet (in the example illustrated in FIG. 2, the front side of a tank), and the imaging unit 280 and the illuminance sensor unit 290 not illustrated in the drawing may be disposed in a range in which a film can be moved by the transfer unit 260. In addition, the transfer unit 260 and the storage unit 270 do not need to be an integrated type as illustrated in FIG. 2 and may be disposed on a wall face or a top face of the tank individually or integrally or may be disposed near the toilet or the like as an independent-type device. In this way, a device in which only the measurement unit 210 is disposed is installed inside the bowl of a toilet or the like, and the other devices may be appropriately installed in a range which does not cause any communication problem, and a device configuration having versatility for the shape of a toilet may be formed.

In addition, a device in which the user identifying unit 220 is disposed may be a device that can be disposed at a position at which the user terminal 300 and the like can be held up such that quick response (QR) code information output by the user terminal 300 held by the user or information output by an integrated circuit (IC) card can be read by the device. In this way, measurement can be performed after a user is identified without inputting user identification information from the user to the measurement device 200 each time of use.

The measurement unit 210 measures a part of fluid information relating to a fluid in reserved water into which urine of a user using the toilet has flown. The user identifying unit 220 has a function of identifying a user using a toilet who is a monitoring target for which a health state is monitored by the health monitoring system 500.

The control unit 230 is a processor having a function of controlling each unit of the measurement device 200. In addition, the control unit 230 can control an input means, for example, buttons, a handle, an infrared sensor, and the like that may be used by a user for manually selecting start of each measurement relating to urination (not illustrated in the drawing). The control unit 230 notifies the measurement unit 210 of input of a measurement start instruction using the input means.

The communication unit 240 includes a reception unit 241 and a transmission unit 242 and has a function of executing communication with the server 100 and each user terminal 300 through the network 400. The communication may be any one of wired communication and wireless communication (for example, a communication system using Wireless Fidelity (Wi-Fi), Bluetooth Low Energy (BLE), ZigBee, or the like), and any communication protocol may be used as long as mutual communication can be executed.

The reception unit 241 has a function of receiving control data and the like from each server 100 and each user terminal 300 in accordance with control of the control unit 230 through the network 400 and transmitting the control data and the like to the control unit 230. More specifically, the reception unit 241 receives user information (for example, ID information and the like) for controlling the user identifying unit 220, dynamic parameter data required for measurements using the measurement unit 210, imaging using the imaging unit 280, and identification using the user identifying unit 220, and the like from the server 100 and transmits the received information to the control unit 230.

The transmission unit 242 has a function of transmitting measurement data and the like to the server 100 and each user terminal 300 through the network 400 in accordance with control of the control unit 230. More specifically, for example, the transmission unit 242 transmits water temperature information, voltage information, environment information, user identification information (including measurement information), illuminance information, and imaging information to the server 100 or each user terminal 300.

The memory unit 250 has a function of storing various programs, data, and parameters required for the measurement device 200 to operate. More specifically, for example, the memory unit 250 stores user information and parameters that are necessary for the operations of the measurement unit 210, the user identifying unit 220, the control unit 230, and the communication unit 240. The memory unit 250 is typically realized by various recording media such as a hard disk drive (HDD), a solid state drive (SSD), a flash memory (a secure digital (SD) memory card), and the like.

The storage unit 270 stores films that produce color reactions for a composition to be detected. In addition, the configuration of the films will be described later. The transfer unit 260 takes a film out of the storage unit 270 and immerses the film that has been taken out in reserved water of the toilet in which urination flows. The imaging unit 280 images a film immersed in the reserved water and generates imaging information relating to the film. The illuminance sensor unit 290 measures illuminance (brightness) of a film surface imaged by the imaging unit 280. The schematic configuration of the measurement device 200 has been described as above.

Next, the server 100 will be described. The server 100 is configured to include a communication unit 110, a control unit 120, and a memory unit 130. In addition, the server 100 may a multistage configuration and, for example, may be composed of a server (relay server) disposed inside a facility in which the measurement device 200 is installed and a server completely covering a specific area including a plurality of facilities or all areas. In addition, a transmission timing of the relay server may be set as (1) being periodically transmitted (for example, for every constant time set with the capacity of the memory unit 130 of the server 100 and the like taken into account), (2) a timing when a memory capacity reaches a threshold of the memory capacity of the memory unit 250 of the measurement device 200, which has been set, or the like.

The communication unit 110 includes a reception unit 111 and a transmission unit 112 and has a function of executing communication with the measurement device 200 and the user terminal 300 through the network 400. The communication may be any one of wired communication and wireless communication, and any communication protocol may be used as long as mutual communication can be executed. The network 400, for example, is a network such as Long Term Evolution (LTE), Local Area Networks (LANs), Wide Area Networks (WANs), Metropolitan Area Networks (MANs), or Integrated Service Digital Networks (ISDNs) or a network such as a wireless LAN, Code Division Multiple Access (CDMA), Bluetooth (registered trademark), satellite communication, or the like and may be any network as long as the server 100 and the measurement device 200 can communicate with each other through it regardless of whether it is a wired network or a wireless network.

The reception unit 111 has a function of receiving measurement data and the like from each measurement device 200 and each user terminal 300 through the network 400 and transmitting the measurement data to the control unit 120 in accordance with control of the control unit 120. In addition, the reception unit (acquisition unit) 111 acquires shape information of a bowl of a toilet, water amount information of reserved water, and environment information relating to a surrounding environment of the measurement unit 210 from the measurement device 200. In addition, the shape information of the bowl of the toilet may be stored in the memory unit 130 in advance or may be stored in a data server or the like, which is not illustrated in the drawing, other than the server 100 and be acquired from the data server or the like. More specifically, the reception unit 111 receives water temperature information of urination containing water, voltage information according to an electric potential difference between electrodes immersed in the urination containing water, user identification information used for identifying a user, illuminance information of the toilet, imaging information acquired by imaging a film after a color reaction using the imaging unit 280, and the like transmitted from the measurement device 200.

The transmission unit 112 has a function of transmitting control data and the like to each measurement device 200 and transmitting data relating to a result of monitoring (an analysis result, a prediction result, and the like) and the like to each user terminal 300 through the network 400 in accordance with control of the control unit 120. More specifically, for example, the transmission unit 112 transmits user information (for example, ID information or the like) used for controlling the user identifying unit 220, dynamic parameter data that is necessary for measurement using the measurement unit 210, imaging using the imaging unit 280, and user identification using the user identifying unit 220, and the like to the measurement device 200. In addition, the transmission unit 112 transmits display data used for displaying monitoring results such as an analysis result relating to compositions of urine analyzed by the analysis unit 122, a prediction result relating to positivity or negativity of a disease predicted by the prediction unit 124, and the like to the user terminal 300.

The control unit 120 is a processor having a function of controlling each unit of the server 100 and is configured to include an interpretation unit 121, an analysis unit 122, a prediction unit 124, and a generation unit 125. The interpretation unit 121 analyzes urination by analyzing a fluid model acquired by modeling a fluid on the basis of at least one of fluid information, shape information of a bowl of a toilet, water amount information of reserved water, and environment information relating to a surrounding environment of the measurement unit 210 measured by the measurement unit 210 of the measurement device 200. The analysis unit 122 analyzes urine compositions of urination on the basis of the imaging information transmitted from the measurement device 200. In addition, the analysis unit 122 includes the correction unit 123, corrects imaging information on the basis of urination information and fluid information acquired as a result of an analysis using the interpretation unit 121, and analyzes urine compositions of urination on the basis of the corrected imaging information. The prediction unit 124 predicts a likelihood of having a disease on the basis of an analysis result acquired by the analysis unit 122. In addition, the prediction unit 124 generates a characteristic vector from the imaging information, identifies the generated characteristic vector using training data, and predicts a likelihood of having a disease on the basis of the identified characteristic vector.

In addition, the generation unit 125 generates display data used for displaying the analysis result and the prediction result as texts, tables, or graphs on a display unit 330 of the user terminal 300 on the basis of at least one of an analysis result acquired by the analysis unit 122 and a prediction result acquired by the prediction unit 124. The transmission unit 112 transmits the generated display data to the user terminal 300. In addition, the display data may be generated by the user terminal 300 to be described later. In such a case, information relating to the analysis result and the prediction result is transmitted from the transmission unit 112 to the user terminal 300.

The memory unit 130 has a function of storing various programs, data, and parameters that are necessary for operating the server 100. More specifically, for example, the memory unit 130 saves and stores fluid information (shape information of a bowl of a toilet, water amount information of reserved water of the toilet, and the environment information), imaging information, weight information, illuminance information, information required for interpretation, an analysis, and the like of user identification information and the like, parameters required for operations of the communication unit 110, the control unit 120, and the memory unit 130, a measurement result, an analysis result, a prediction result, and the like in various databases (hereinafter, referred to as "DBs").

In addition, a method of storing and managing data is not limited to the method using DBs, and data may be stored by saving data in various settings files such as definition files, parameter files, temporary files, and the like (hereinafter, referred to as "settings files"). The memory unit 130 is typically realized by various recording media such as an HDD, an SSD), a flash memory (SD memory card) and the like. In addition, various DBs will be described later with reference to FIG. 11. The configuration of the server 100 has been described as above.

Next, the configuration of the user terminal 300 will be described. As illustrated in FIG. 3, the user terminal 300 is configured to include a communication unit 310, a control unit 320, a display unit 330, and a memory unit 340. Each unit of the user terminal 300 may be configured to be included in the health monitoring application or may be built in a circuit of the user terminal 300.

The communication unit 310 includes a reception unit 311 and a transmission unit 312 and has a function of executing communication with the server 100 and each measurement device 200 through the network 400. The communication may be any one of wired communication and wireless communication, and any communication protocol may be used as long as mutual communication can be executed.

The reception unit 311 has a function of receiving display data and the like from each server 100 and each measurement device 200 and transmitting the display data and the like to the control unit 320 through the network 400 in accordance with control of the control unit 320. More specifically, the reception unit 311, for example, receives display information including a result of an analysis of urine from the server 100. In addition, the control unit 320 is a processor having a function of controlling each unit of the user terminal 300.

The transmission unit 312 has a function of transmitting various kinds of information input by a user, user identification information such as QR code information, and the like to the server 100 and each measurement device 200 through the network 400 in accordance with control of the control unit 320.

The display unit 330 has a function of displaying display data and the like received from the server 100 or the measurement device 200. More specifically, for example, the display unit 330, as illustrated in FIG. 3, displays display data representing monitoring results such as a measurement result including measured values, normality/abnormality, and the like relating to measured urination, an analysis result relating to analyzed urine compositions, a predicted result representing positivity/negativity of a predicted disease, and the like using texts, tables, graphs, or the like. The results may be displayed in units of display designated by a user such as in units of days, in units of weeks, in units of months, or the like. In addition, the display unit 330 may include an input means for a user and, for example, allow the user to input user identification information (for example, a name, age, sex, height, weight, and the like). In addition, the display data may be generated by the control unit 320 on the basis of an analysis result and a prediction result transmitted from the server 100.

The memory unit 340 has a function of storing various programs, data, and parameters that are necessary for the user terminal 300 to operate. More specifically, for example, the memory unit 340 stores the user identification information and parameters that are necessary for the operations of the communication unit 310, the control unit 320, the display unit 330, and the memory unit 340. The memory unit 250 is typically realized by various recording media such as an HDD, an SSD, a flash memory (SD memory card), and the like. An overview of the user terminal 300 has been described as above.

Next, an analysis of urine using a film will be described in detail. First, the transfer unit 260 that is a mechanism immersing a film in urination-containing water will be described. FIG. 4 is a schematic diagram of the transfer unit 260 according to one aspect of the present invention, FIG. 4A is a front-side perspective view, FIG. 4B is a rear-side perspective view, and FIG. 4C is a schematic diagram of an internal structure. The transfer unit 260 includes an upper rod 261, a lower rod 262, a first moving rod 263*a*, and a second moving rod 263*b*. As illustrated in FIG. 4, the upper rod 261, the lower rod 262, the first moving rod 263*a*, and the second moving rod 263*b* are positioned approximately in parallel with each other in the longitudinal direction. In addition, the transfer unit 260 includes a clamping unit 264, and the clamping unit 264 clamps a filter using opening/closing parts of an upper clamping member 2611 and a lower clamping member 2621 having one ends connected through a connection shaft 265. Here, the other ends of the upper clamping member 2611 and the lower clamping member 2621, which are not connected through the connection shaft 265, serve as an opening/closing part of the clamping unit 264. In addition, although the shapes of the upper clamping member 2611 and the lower clamping member 2621 are not limited to those illustrated in the example of the drawing, by using a structure having many holes as illustrated in the drawing, the weight of the clamping unit 264 can be decreased.

Furthermore, the transfer unit 260 includes an upper drive unit 2616, a lower drive unit 2626, and a moving drive unit 2636. The upper drive unit 2616 drives the upper rod 261 to which the upper clamping member 2611 is connected in a longitudinal direction of the upper rod 261. The lower drive unit 2626 drives the lower rod 262 to which the lower clamping member 2621 is connected in a longitudinal direction of the lower rod 262. In addition, the moving drive unit 2636 drives the first moving rod connected to the upper clamping member 2611 through the connection shaft 265 and the second moving rod 263*b* connected to the lower clamping member 2621 through the connection shaft 265 in longitudinal directions of the first moving rod 263*a* and the second moving rod 263*b*. In addition, each drive unit is controlled by the control unit 230 of the measurement device 200. Here, the transfer unit 260 may be connected to the control unit 230 in a wired manner and controlled or may include a reception unit not illustrated in the drawing and be controlled wirelessly by the control unit 230.

The upper drive unit 2616, for example, is realized by a stepping motor or the like, and an upper pinion 2615 is connected thereto. In addition, the upper rod 261, for example, is realized by a rack. The upper pinion 2615 is engaged with the upper rod (rack) 261, and, when the upper drive unit 2616 rotates the upper pinion 2615, the upper rod 261 is driven in the longitudinal direction. The upper rod 261 is connected to the upper clamping member 2611 through an upper bracket 2612.

The lower drive unit 2626, for example, is also realized by a stepping motor or the like, and a lower pinion 2625 is connected thereto. In addition, the lower rod 262, for example, is realized by a rack. The lower pinion 2625 is engaged with the lower rod (rack) 262, and, when the lower drive unit 2626 rotates the lower pinion 2625, the lower rod 262 is driven in the longitudinal direction. The lower rod 262 is connected to the lower clamping member 2621 through the lower bracket 2622.

The moving drive unit 2636, for example, is also realized by a stepping motor or the like, and a first moving pinion 2635*a* and a second moving pinion 2635*b* are connected thereto. The first moving rod (rack) 263*a* is engaged with the first moving pinion 2635*a*, and the second moving rod (rack) 263*b* is engaged with the second moving pinion 2635*b*, and, when the moving drive unit 2636 rotates the first moving pinion 2635*a* and the second moving pinion 2635*b*, the first moving rod 263*a* and the second moving rod 263*b* are moved in a longitudinal direction.

The upper drive unit 2616, the lower drive unit 2626, and the moving drive unit 2636 are housed in a housing unit 267. The housing unit 267, for example, is realized by a casing configured by a lid and a main body, and it is preferable to seal between the lid and the main body using an O-ring or the like for improving a waterproof property thereof. In addition, the other pinions 2613, 2614, 2623, 2624, 2633*a*, 2633*b*, 2634*a*, and 2634*b* are pinions that achieve the role of a guide at the time of moving by supporting the housing unit 267.

In addition, a state illustrated in FIG. 4 represents an initial position of the clamping unit 264. The transfer unit 260 is covered with a cover not illustrated in the drawing on a part other than the clamping unit 264, and screws W1 to W4 lock the cover not illustrated in the drawing. By using this cover, the waterproof property and the dustproof property can be improved. In addition, as a material configuring each unit of the transfer unit 260, plastic may be used. In such a case, the entire weight of the transfer unit 260 can be decreased, and electric power used for driving the clamping unit 264 in the vertical direction can be reduced. In addition, a load at an installation site can be reduced, and carrying can be easily performed.

Figure 5A:
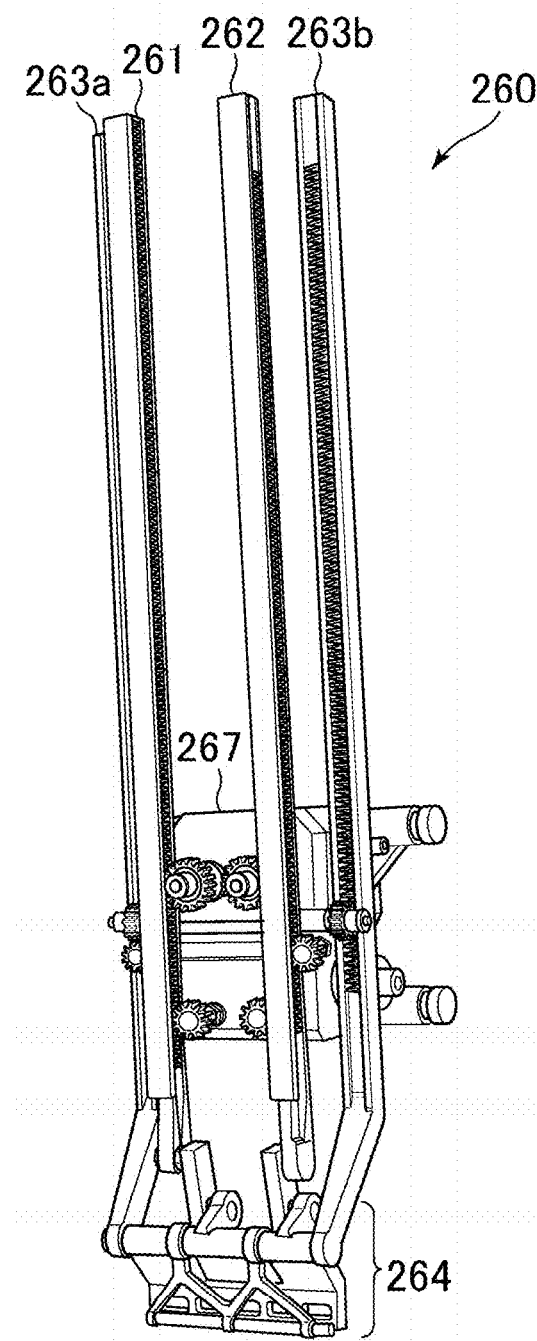
FIG. 5A is a schematic diagram illustrating driving of a transfer unit according to one aspect of the present invention, illustrating a state in which a clamping unit is raised.
Figure 5B:
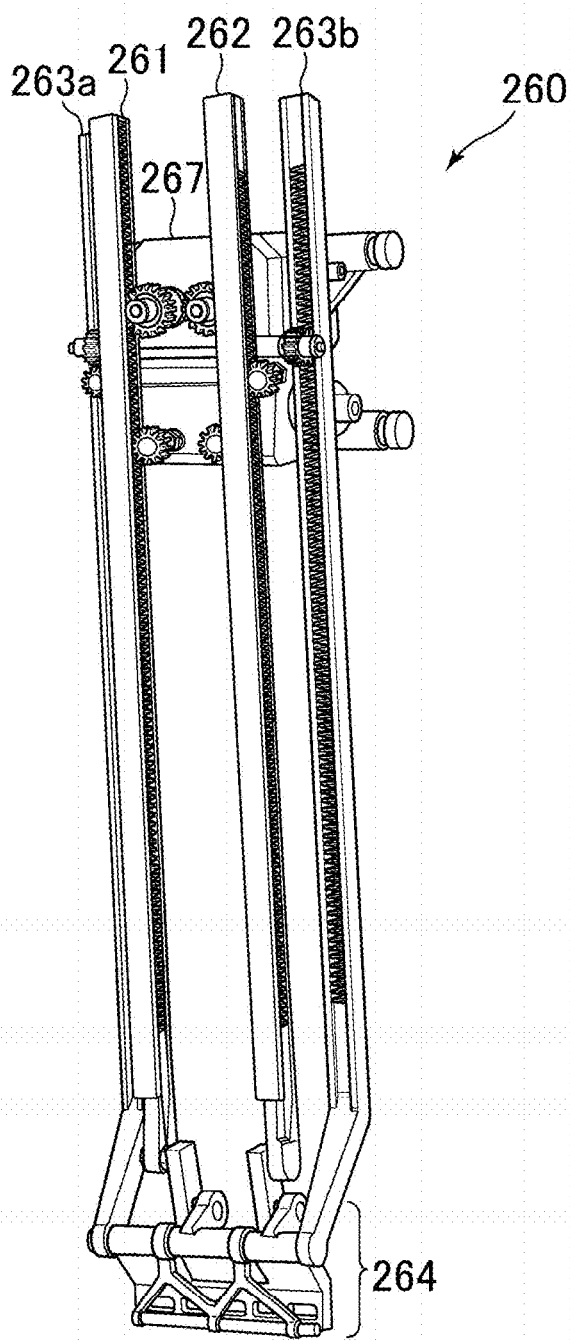
FIG. 5B is a schematic diagram illustrating driving of a transfer unit according to one aspect of the present invention, illustrating a state in which the clamping unit is lowered.

Next, a method of driving the transfer unit 260 will be described with reference to FIGS. 5 and 6. FIG. 5 is a schematic diagram illustrating driving of the transfer unit 260 according to one aspect of the present invention, FIG. 5A is a diagram illustrating a state in which the clamping unit 264 is raised, and FIG. 5B is a diagram illustrating a state in which the clamping unit 264 is lowered. By driving the upper drive unit 2616, the lower drive unit 2626, and the moving drive unit 2636 from an initial state illustrated in FIG. 5A such that relative positional relations among the upper rod 261, the lower rod 262, the first moving rod 263*a*, and the second moving rod 263*b* are maintained, as illustrated in FIG. 5B, the position of the clamping unit 264 can be moved in the longitudinal direction of the rod without the shape of the clamping unit 264 changing.

FIG. 6 is a schematic diagram illustrating a positional relation between opening/closing of the clamping unit 264 and each of rods 261, 262, 263*a*, and 263*b* in the transfer unit 260 according to one aspect of the present invention. FIG. 6 schematically illustrates a relative positional relation of each rod and a relation with the state of the clamping unit 264. First, a state illustrated in FIG. 6A is assumed to be an initial state. When the upper rod 261 is moved in a downward direction with respect to the other rods 262, 263*a*, and 263*b* from this state as illustrated in FIG. 6B, the upper clamping member 2611 rotates in the direction of an arrow, and the clamping unit 264 opens. In addition, when the lower rod 262 is moved in a downward direction with respect to the other rods 261, 263*a*, and 263*b* from the initial state illustrated in FIG. 6A, the lower clamping member 2621 rotates in the direction of an arrow, and the clamping unit 264 opens. Furthermore, when the first moving rod and the second moving rod 263*a* and 263*b* are moved in a downward direction with respect to the other rods 261 and 262 from the initial state illustrated in FIG. 6C as illustrated in FIG. 6D, the entire clamping unit 264 rotates about the connection shaft as its rotation shaft.

As described above, according to one aspect of the present invention, the transfer unit 260, as illustrated in FIG. 5, moves a film, to be described later, by clamping and rotating the film, as illustrated in FIG. 6, by changing the height of the clamping unit 264. At this time, only the positional relation among the rods may be changed in opening/closing and rotation of the clamping unit 264, whereby control can be simplified. In addition, depending on the driving, the clamping unit 264 may be open/closed or rotated while changing the position of the clamping unit 264. For this reason, a time required for the transferring of a film can be shortened.

In addition, the transfer unit 260 includes an upper drive unit 261G, a lower drive unit 262G, and a moving drive unit 263G and includes a housing unit 267 that houses the drive units. In addition, it is preferable to dispose the housing unit 267 at a position separate from the clamping unit 264 by a predetermined distance in a case in which a film clamped by the clamping unit 264 is immersed into reserved water. In this way, by disposing drive units driving the rods to be close to each other, a size of the transfer unit 260 can be configured to be small. In addition, a wiring process can be simplified. Furthermore, in a case in which the drive units are housed together in the housing unit 267 and the clamping unit 264 is caused to approach reserved water, by separating the clamping unit 264 and the housing unit 267 from each other, the waterproof property of the drive units is improved, and the durability can be improved.

In addition, for example, in order to open/close or rotate the clamping unit 264, disposing a drive unit such as a motor or the like in the clamping unit 264 may be considered. However, in a case in which a drive unit such as a motor or the like is disposed in the clamping unit 264, the weight of the clamping unit 264 increases, and a load is applied for driving. In addition, since the clamping unit 264 is a part approaching reserved water, there is a problem also in the waterproof property of the drive unit. In contrast to this, according to the present invention, since the drive unit is separate from the clamping unit 264, the weight of the clamping unit 264 is decreased, and the load applied to the driving decreases, and the drive unit is not close to reserved water such that an additional plan for a waterproof property does not need to be set up. For this reason, there are also advantages of reducing costs and labor for manufacturing.

Figure 7A:
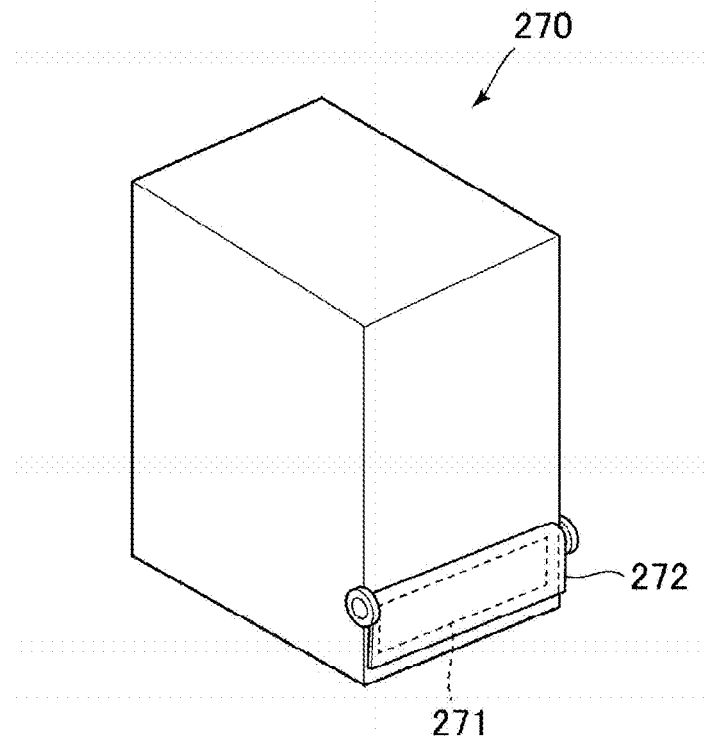
FIG. 7A is a schematic diagram of a storage unit according to one aspect of the present invention in a perspective view.
Figure 7B:
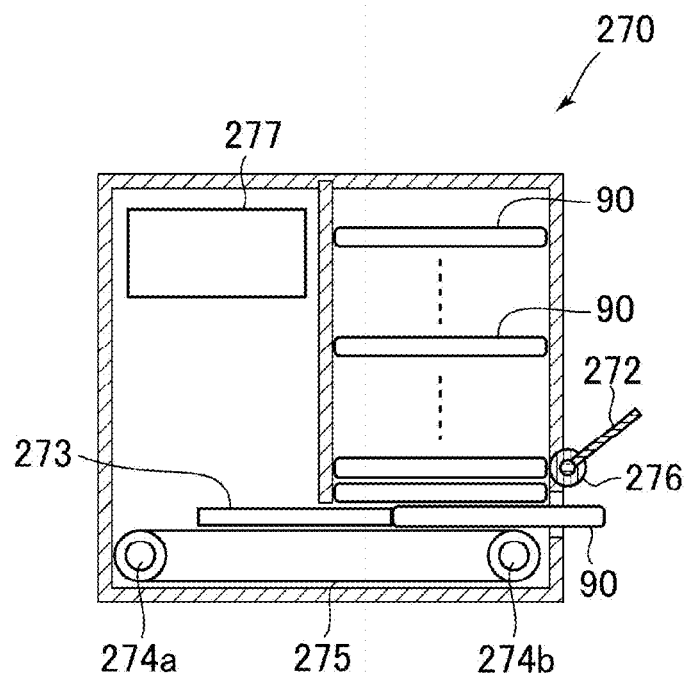
FIG. 7B is a schematic diagram of a storage unit according to one aspect of the present invention in a perspective projection as viewed from the side.

Next, the storage unit 270 will be described with reference to FIG. 7. FIG. 7 is a schematic diagram of the storage unit according to one aspect of the present invention, FIG. 7A is a perspective view, and FIG. 7B is a perspective projection as viewed from the side. The storage unit 270 stores a film that produces a color reaction for a composition to be detected, and, in the health monitoring system 500 according to one aspect of the present invention, the film is immersed in reserved water or urination-containing water, and urine compositions are analyzed on the basis of a color reaction of a reagent loaded in the film.

As illustrated in FIG. 7, the storage unit 270 includes an opening part 271, an extrusion part 273 that extrudes a film 90 from the opening part 271, a lid part 272 that covers the opening part 271, and a drive unit (not illustrated in the drawing) that drives the extrusion part 273 and the lid part 272. In addition, the drive unit may be disposed inside or outside the storage unit 270. Furthermore, the storage unit 270 and each member included therein, for example, may be realized using plastic or the like. In such a case, in order to maintain the quality of the film 90, it is preferable to realize them using a material having low hygroscopicity. In addition, the shape of the storage unit 270 is one example and is not limited thereto.

As illustrated in FIG. 7B, a plurality of films 90 are stacked and housed inside the storage unit 270. The extrusion part 273 has a height and a width that are about a thickness and a width of the film 90 and is disposed on the moving mechanism 275. Various forms of the moving mechanism 275 may be considered, but, for example, the moving mechanism 275 may be realized by a belt conveyer or a moving mechanism using a suction force of vacuum or the like. In addition, the opening part 271 has a size that is slightly larger than the thickness and the width of the film 90 and enables extraction of one film 90 and is covered with the lid part 272 in the initial state. This lid part 272 covers the opening part 271 so as to prevent the state of films 90 inside the storage unit 270 from degrading due to moisture absorption, dust, and the like. In addition, in the example illustrated in the drawing, although the lid part 272 is installed such that it rises, the lid part may be installed such that it descends or may be installed in the form of double-hinged doors.

When the extrusion part 273 is moved by the moving mechanism 275, the lid part 272 rotates around a shaft 276 as its rotation shaft in association with the moving mechanism 275 and exposes the opening part 271. Then, a film 90 is extruded from the opening part 271 by the extrusion part 273. In addition, the extrusion part 273 may extrude the whole film 90 to the outside of the storage unit 270 or may extrude a part thereof. For example, the extrusion part 273 may extrude a film 90 positioned in a lowermost part of the storage unit 270 up to a position at which the film can be clamped by the clamping unit 264 outside the storage unit 270.

In this way, a plurality of films are stacked in the storage unit 270, and the films are extruded only when urination is measured. Accordingly, urination can be measured in a simplified manner without preparing a film every time when measurement is performed. In addition, since the opening part 271 is closed by the lid part 272, a measurement result having high reliability can be acquired without degrading the durability of films.

When a film 90 is extruded, the extrusion part 273 is driven such that it returns to the position of the initial state. When the extrusion part 273 returns up to the position of the initial state, the stacked films descend up to an extruded position in accordance with a gravitational force, and the extrusion part 273 can extrude the next film 90 from the opening part 271 in accordance therewith. In addition, the film 90 may descend up to the extruded position in accordance with the weight thereof and, for example, a pressing mechanism such as a spring may be disposed in the storage unit 270, and a film 90 may be moved up to the extruded position. In a case in which a pressing mechanism is disposed, the direction of the film 90 does not need to be considered when the storage unit 270 is installed, and accordingly, the degree of freedom of an installation site can be raised.

In addition, a dehumidification mechanism 277 that includes at least one of a dehumidifier and a dehumidification module is further stored inside the storage unit 270. Accordingly, the durability and the quality of the films 90 can be maintained. In addition, it is preferable that the dehumidification mechanism 277, as illustrated in FIG. 7B, is disposed in a space in which the effect of dehumidification is improved on a side of the film 90 that is not brought into contact with the wall face in which the opening part 271 is formed in the storage unit 270. The reason for this is that the film 90 is clamped by the clamping unit 264 on the opening part 271 side, and accordingly, the opening part 271 side of the film 90 can allow some degradation of durability. In addition, it is preferable that the dehumidification mechanism 277, for example, is delimited from the films 90 to have a structure such as a mesh shape having good air permeability.

In addition, depending on the dehumidification mechanism 277, degradation of a reagent on the film 90 can be suppressed without disposing the lid part 272. This is because, for example, the dehumidification mechanism 277 that can be stored is different in accordance with the size and the installation site of the storage unit 270, and accordingly, there are also cases in which the lid part 272 may not be disposed depending on the performance of the dehumidification mechanism 277. In a case in which the lid part 272 is not disposed, there is an advantage in that the structure of the storage unit 277 is further simplified, and the manufacturing thereof can be easily performed.

In addition, it is preferable that the dehumidification mechanism 277 is replaced when films 90 are newly supplemented after the films 90 are used up. Alternatively, in a case in which the films 90 are used up, the entire storage unit 270 may be replaced. Accordingly, a validity period and the like of the dehumidification mechanism 277 do not need to be managed separately from the films, and a health monitoring system enabling easy operation of the service and convenient use can be provided.

Here, operations of the transfer unit 260 and the storage unit 270 described above when measurement is performed using the film 90 will be described with reference to FIG. 8.

As illustrated in FIG. 8A, a film 90 having a part or the entirety extruded from the storage unit 270 by the extrusion part 273 is clamped by the clamping unit 264 of the transfer unit 260. Subsequently, as illustrated in FIG. 8B, the transfer unit 260 moves the clamping unit 264 in the downward direction and immerses a film 90 in reserved water or urination-containing water. The transfer unit 260 stops the clamping unit 264 in the state in which the film 90 is immersed in the reserved water or the urination-containing water and causes a reagent loaded in the film 90 to produce a color reaction. When the color reaction of the reagent loaded in the film 90 is completed, the transfer unit 260 moves the clamping unit 264 in the upward direction. Thereafter, the transfer unit 260 moves or rotates the clamping unit 264 in the upward direction up to a position at which the film 90 after the reaction can be imaged by the imaging unit 280. In other words, it is preferable that the transfer unit 260 is disposed at a position at which a film 90 can be extruded from the storage unit 270, and the film 90 clamped by the clamping unit 264 can be imaged by the imaging unit 280. At that time, since the length of each rod in the transfer unit 260 can be adjusted at the time of design, there is a degree of freedom in the arrangement of each unit and the type of installable toilet. In addition, the measurement device 200 may be realized to be integrated with a toilet in advance instead of being added to an existing toilet, whereby the space can be further saved.

In addition, the lengths of the rods do not need to be the same. For example, a case in which a moving range and a rotation range of the clamping unit 264 are restricted in advance such as a case in which an installation site is determined in advance or a case in which the measurement device is manufactured to be integrated with a toilet may be considered, and, in such a case, the length of each rod may be changed in accordance with the moving range and the rotation range of the clamping unit 264.

Next, an analysis using a film will be described in detail. The film 90 is a material to which a reagent can be added and which can color-react with a specific composition of urine and which may be composed of a polymer composition such as a composite resin or a fiber such as paper or a cloth. In addition, although it is preferable that the film 90 is transparent or while, the film is not limited thereto. Furthermore, although the film 90 is extruded by the extrusion part 273 and thus is preferably water-soluble such that it dissolves inside reserved water, as will be described later, while having a certain degree of rigidity, the film is not limited thereto depending on the use environment.

In addition, for example, in a case in which an immunochromatography method is used as the assay method, although the film 90 is configured to include a sample pad, a conjugate pad, a test line (detection line), a control line, a membrane, an absorption pad, and the like, the film is not limited thereto.

FIG. 9 is a diagram schematically illustrating one example of the configuration of the film 90 and the reagent 70. As illustrated in FIG. 9, as the film, a film 90 can be configured using a top film 60 used for protecting the surface of a reagent 70 and a support body film 80 used for loading the reagent (for a support body for the reagent) by interposing the reagent between the top film 60 and the support body film 80. Regarding the top film 60, (1) the top film 60 is dissolved at the time of measurement using a water-soluble film and (2) a mechanism stripping the top film 60 is built into the storage unit 270 or the transfer unit 260, and the top film 60 is stripped immediately before measurement may be considered. According to (1) or (2), the reagent can be protected until immediately before measurement, and degradation of the reagent can be prevented. In addition, without using the top film 60, (3) by configuring the storage unit 270, in which films 90 are stored, to have a structure having a high level of airtightness using the lid part 272 or the like as described above, the amount of air brought into contact with the film 90 immediately before measurement is decreased greatly, and the degradation of the reagent can be prevented.

After imaging of a color reaction of the reagent performed by the imaging unit 280 is completed, the clamping unit 264 moves the film 90 to a place in which the film 90 is caused to fall into the reserved water and releases the film 90. Therefore, the film 90 falls into reserved water or urination-containing water, and the film 90 that is water-soluble is dissolved in the reserved water or the urination-containing water. In addition, when flushing is performed (at the time of washing the toilet in which urination or the like is caused to be flushed using water), the film 90 is discarded together with the reserved water or the urination-containing water. In this way, the film is extracted and is discarded in the reserved water every time when measurement is performed, and accordingly, a health monitoring system that is hygienic and has a high degree of convenience can be provided without requiring efforts of a user or a measuring person. Alternatively, a space in which a film can be hygienically stored after measurement may be disposed in the device.

In addition, according to one aspect of the present invention, urination is analyzed on the basis of fluid information relating to a fluid in reserved water into which urination of a user using a toilet has flown, and the accuracy of a result of the analysis using a film can be improved on the basis of urination information of the analyzed urination. Hereinafter, the embodiment will be described.

As illustrated in FIG. 3, the measurement unit 210 of the measurement device 200 includes an electrode unit 211 and a temperature measuring unit 212 and, for example, as illustrated in FIG. 2, the electrode unit 211 and the temperature measuring unit 212 are installed to be immersed partly in reserved water inside a bowl of a toilet.

The electrode unit 211 has a function of measuring an electromotive force (an electric potential difference; a voltage value) according to an electrolyte and a current value flowing between the electrodes immersed in urination-containing water for a specific composition in urine that is the electrolyte using two or more electrodes and generating voltage information. In addition, the "voltage information" represents information relating to an electromotive force (an electric potential difference; a voltage value) according to a specific composition (electrolyte) in urine that is generated using the electrodes of the electrode unit 211. More specifically, for example, the electrode unit 211 is configured by two or more electrodes, a potentiometer, and an ampere meter for measuring a concentration of a specific composition in urine. In the electrode unit 211, for example, one electrode is set as a reference electrode, and the other electrode is set as a working electrode, the electrodes are immersed in urination containing water, and an electromotive force difference between the working electrode responding to a concentration (activity) of a urine composition, which is a target to be analyzed, of the urination-containing water and the reference electrode is measured using the potentiometer. Voltage information is generated on the basis of a result of the measurement using the electrode unit 211, and the generated voltage information is transmitted from the transmission unit 242 to the server 100.

In addition, although an example using an ion selective electrode method has been described above, an oxygen electrode method (glucose oxidase (GOD)) may be used, and, by adding an electrode that is an opposite electrode, an electrode method using three electrodes may be used. Accordingly, a concentration and the like of a specific composition in urine can be measured on the basis of the generated voltage information.

The temperature measuring unit 212 has a function of measuring a temperature of reserved water inside a bowl of a toilet or a temperature of urination-containing water and generating water temperature information. The temperature measuring unit 212, for example, is composed of a thermistor, an oscillator, and a counter and measures a temperature by outputting a change in the resistance value according to a change in temperature using the thermistor, converting the change in the resistance value into a frequency using the oscillator, and measuring the frequency using the counter. The water temperature information is transmitted from the transmission unit 242 to the server 100.

The interpretation unit 121 of the server 100, as described above, has a function of analyzing urination by analyzing a fluid model acquired by modeling an area in which a fluid flows on the basis of fluid information. More specifically, the interpretation unit 121, for example, calculates the amount of urine by analyzing the fluid in the vicinity of the measurement unit 210 using a fluid model acquired by modeling a fluid flowing in the vicinity of the measurement unit 210 on the basis of at least one of the shape information of a bowl of a toilet, water amount information of reserved water inside the bowl of the toilet, the water temperature information, and the like. In addition, the interpretation unit 121 may analyze urine by adding at least one piece of information relating to toilet environments such as information of the amount of detergent and the like and composition information of a detergent and the like to the shape information of the bowl of the toilet, the water amount information of reserved water inside the bowl of the toilet, and the water temperature information and perform modeling or the like of the fluid on the basis of these. Accordingly, it is not necessary to measure the amount of urine by sampling only urine or measure the amount of urine on the basis of the rate of change in the water level using a measurement device or the like installed in the bowl or a water drainage pipe of the toilet, and a health monitoring system that can be conveniently used by a user can be provided.

The modeling of the fluid, for example, is assumed to build a prediction model predicting changes and final convergence of water temperature of the reserved water and the urination-containing water on the basis of the water temperature information generated from the measured water temperatures of the reserved water and the urination-containing water using a regression model according to a support vector machine (SVM) or the like and perform an analysis. In addition, the analysis may be performed by combining a data structure led using a kernel method with the SVM in the regression analysis. Furthermore, as another example, building a regression model using an regression analysis according to a Markov Chain Monte Carlo (MCMC) method and performing an analysis may be considered. In addition, other than these, as an example of modeling a fluid area using a fluid simulation, using a finite element method or a computational fluid dynamics (CFD) method may be considered.

The correction unit 123 has a function of correcting voltage information on the basis of the urination information including the water amount information and the amount of urine. More specifically, for example, the correction unit 123 calculates a degree of dilution by dividing the amount of urine by a sum of the water amount and the amount of urine and corrects the voltage information using the degree of dilution. In this way, the voltage information with dilution according to the reserved water inside the bowl of the toilet and the like taken into account can be acquired, and urine compositions can be analyzed.

In addition, the correction unit 123 has a function of correcting imaging information on the basis of the illuminance information. Here, the "illuminance information" is information representing illumination (brightness) (lx) of a film surface and is information transmitted by the illuminance sensor unit 290 of the measurement device 200. More specifically, for example, the correction unit 123 performs correction by adjusting the brightness levels of RGB values to appropriate values on the basis of the illuminance information. In this way, RGB values can be acquired which take the influence of lighting into account, and color measurement with a high accuracy can be performed.

As described above, the analysis unit 122 has a function of analyzing urine compositions on the basis of the imaging information or the corrected imaging information (hereinafter, referred to as "imaging information (after correction))". More specifically, for example, the analysis unit 122 measures a color of a color reaction of a specific composition in urine for a reagent on the basis of the imaging information (RGB values) and analyzes the specific composition in the urine corresponding to the color or the concentration thereof. In addition, in order to generate display data used for displaying a result of the analysis in the user terminal 300, the analysis unit 122 transmits the result of the analysis to the control unit 120. Accordingly, an analysis of a specific composition in urine according to a bioassay method (an immunochromatography method or the like) can be realized in a simplified manner automatically without a person and instead of visual observation or the like performed by a person.

Figure 12:
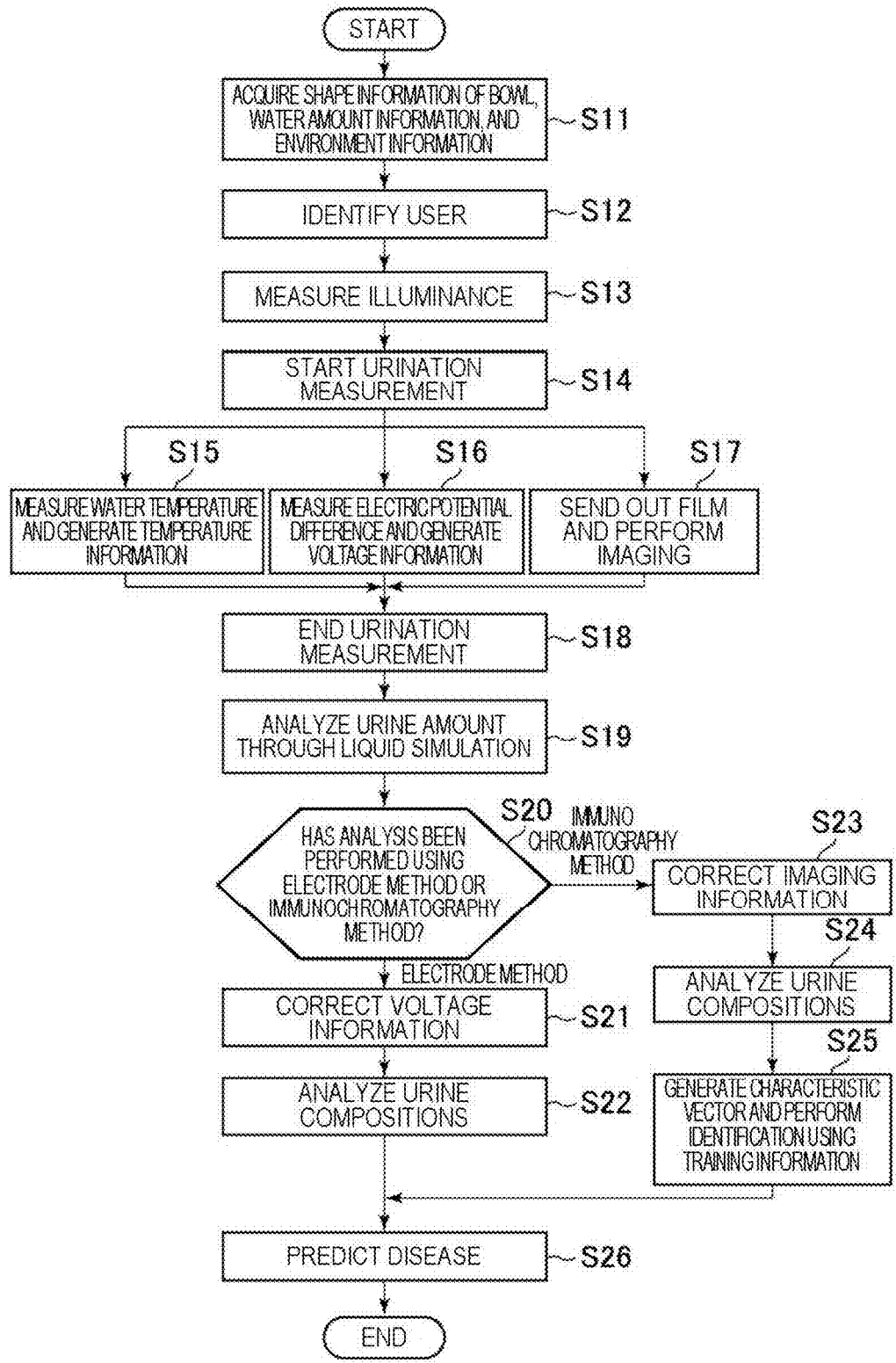
FIG. 12 is a flowchart illustrating one example of a process executed by a health monitoring system according to one aspect of the present invention.

In addition, the analysis unit 122 also has a function of analyzing urine compositions on the basis of the voltage information or the corrected voltage information (hereinafter, referred to as "voltage information (after correction)"). More specifically, the analysis unit 122, for example, analyzes molecule concentrations of compositions such as chloride, glucose, potassium, sodium, urea, and the like in urine on the basis of the voltage information (after correction). In addition, as illustrated in FIG. 12, a ph value can be also analyzed. Accordingly, even in a case in which urination is diluted with reserved water, an analysis with a high accuracy can be performed. In addition, the analysis unit 122 transmits a result of the analysis to the control unit 120 for generating display data used for displaying the result of the analysis in the user terminal 300.

The prediction unit 124 has a function of predicting a likelihood of having a disease of the user on the basis of the urination information of the analyzed urine. More specifically, for example, the prediction unit 124 predicts a likelihood of having a disease of the user on the basis of a specific composition in the analyzed urine (more specifically, for example, a concentration of the composition or the like). As one example, as illustrated in FIG. 11, a sugar urine value is calculated by analyzing the concentration of glucose in the urine, and it is predicted whether diabetes is positive or negative (details will be described later). In addition, FIG. 11 illustrates an example of association between a result of measurements using the other measurement units 210 and a result of an analysis using the analysis unit 122 (referred to as a "measurement/analysis result) and information of a disease predicted on the basis of the measurement/analysis result and the like. A prediction denoted in the example of the association may be included in the prediction using the prediction unit 124. In addition, the prediction unit 124 transmits a result of the prediction to the control unit 120 for generating display data used for displaying the result of the prediction in the user terminal 300.

Here, in a prediction using the prediction unit 124, (1) predicting using a threshold and (2) a prediction using machine learning can be used. As one example, in the prediction (1), the prediction unit 124 predicts a likelihood of having a disease on the basis of a comparison between a measurement result and a threshold stored in the memory unit 130 and, for example, determines a normality (or negativity) in a case in which the measurement result is within the threshold and determines an abnormality (or positivity) in a case in which the measurement result exceeds the threshold. In the prediction (2), a characteristic quantity of the measurement result is extracted, and a characteristic vector is generated on the basis of the characteristic quantity. The generated characteristic vector can be used for identification using dictionary data (data generated using a plurality of cases of sets of a measured value and a test result associated with the measured value (a result on positivity or negativity of a disease based on an analysis result and a prediction result and the like) and data used as training data (teacher data) in machine learning) as a reference and predicting a likelihood of having a disease on the basis of a result of the identification. In addition, as a technique for the machine learning, a neutral network (perceptron), an SVM, or the like may be used. Accordingly, the prediction accuracy of the prediction unit 124 can be improved using a learning effect of the machine learning.

In addition, according to one aspect of the present invention, red, green, and blue (RGB) values of colors according to color reactions of a test line and a control line according to urination-containing water absorbed in a sample pad in the film 90 are imaged by the imaging unit 280. The imaging information (the read RGB values) are transmitted to the server 100, and the analysis unit 122 measures a color generated by the color reaction on the basis of the imaging information. Accordingly, a color can be measured with the costs reduced more than that of a case in which a wavelength and the like are read using a spectroscope or the like. At this time, although it may be assumed that noise is included, by correcting an analysis result on the basis of the voltage information and the illuminance information using the correction unit 123 of the server 100, the noise can be eliminated.

Here, there is a problem in that the conventional technologies disclosed in Patent Documents 1 and 2 cannot be applied to an inspection method of forming a composite through an antigen-antibody reaction by adding a test body to a pad, further combining the composite with an antibody of a different type as a composite, and determining positivity/negativity of pregnancy or a disease in accordance with the reaction (for example, color development or the like) using an antigen-antibody reaction such as an immunochromatography method.

The health monitoring system according to the present invention further includes the film 90, of which a color changes in accordance with a composition of reserved water into which urination has flown, and the imaging unit 280 that generates imaging information by imaging the film 90, in which the correction unit 123 corrects the imaging information on the basis of urination information including water amount information and the amount of urine of the urination, and the analysis unit 122 analyzes urine compositions on the basis of the corrected imaging information and thus can also be applied to an inspection method using an antigen-antibody reaction such as an immunochromatography method and can perform more measurements than a conventional urination information measuring device installed in a toilet.

In addition, in a case in which an input of measurement start from a user is transmitted by the input means included in the control unit 230, the measurement unit 210 can cause the electrode unit 211, the imaging unit 280, the illuminance sensor unit 290, and the temperature measuring unit 212 to start measurements by being triggered upon the transmission.

In addition, when at least one of the temperature information (for example, water temperature of reserved water or urination-containing water) generated by the electrode unit 211 and voltage information (for example, an electric potential difference) generated by the temperature measuring unit 212 reaches a predetermined threshold, the measurement unit 210 can automatically start or end the measurement of each unit configuring the measurement unit 210. In addition, the measurement unit 210 can automatically start or end the measurement on the basis of a result of detection acquired by an infrared sensor (not illustrated in the drawing), which can detect presence/absence of a user, disposed in the measurement device 200. Furthermore, the measurement unit 210 may automatically end or start the measurement on the basis of a pressure sensor (not illustrated in the drawing) disposed in a toilet seat. Accordingly, the user can start measurement during an ordinary urination action without performing an operation of selecting start or end for every start or end of measurement, and a measurement device that is convenient to use can be provided. In addition, in a case in which measurement is started on the basis of temperature information, for example, start of measurement is determined on the basis of a change in the temperature of water inside the toilet before and after the start of a user's urination action. For example, in a case in which the temperature of water inside the toilet rises in accordance with urination of a user, measurement is started.

In addition, the measurement unit 210 may automatically start measurement by being triggered upon completion of a user identification process of the user identifying unit 220. Furthermore, the measurement unit 210 may set a threshold for each measurement item and end measurement by being triggered upon acquisition of data reaching the threshold. In addition, the measurement unit 210 may manually start or end measurement in accordance with an operation input detected by the user terminal 300. Furthermore, a human detection sensor (not illustrated in the drawing) may be disposed in the measurement device 200, measurement may be started by being triggered upon detection of an indication of a person using infrared rays or the like of the human detection sensor, or measurement may be ended by being triggered upon detection of absence of an indication of a person. In addition, the measurement unit 210 may automatically end or start measurement on the basis of a pressure sensor (not illustrated in the drawing) disposed in a toilet seat. For example, the measurement unit 210 may automatically start measurement in a case in which the pressure sensor detects a pressure and may automatically end measurement in a case in which no pressure is detected.

For example, the user identifying unit 220, as illustrated in FIG. 2, is connected to the measurement unit 210 using a wired line such as a cable and may include a suction means for an earthenware device such as a tank such that it is mounted on a tank storing washing water and may include any other mounting means.

More specifically, the user identifying unit 220, for example, identifies a user by reading information (for example, a QR code (registered trademark)) used for uniquely identifying a user which is output by a health monitoring application mounted in the user terminal 300 owned by the user (hereinafter, information used for identifying a user will be referred to as "user identification information"), magnetic information used for uniquely identifying a user of an IC card owned by the user, and information (for example, reception signal intensity information, radiowaves reception intensity information, and the like) used for uniquely identifying a user of Worldwide Interoperability for Microwave Access (WiMAX), a wireless local area network (LAN) such as Wireless Fidelity (WiFi) and Bluetooth.

The user identifying unit 220 identifies a user, for example, by reading a QR code or a bar code displayed in the display unit 330 of the user terminal 300. In this case, the user identifying unit 220 has a function of reading (scanning) a QR code or a bar code. The user, for example, displays a QR code or a bar code in the display unit 330 of the user terminal 300 and causes the user identifying unit 220 of the measurement device 200 to read the code.

In addition, the user identifying unit 220 may identify a user by reading magnetic information from an IC card owned by the user or an RF tag included in the user terminal using a radio frequency identifier (RFID) technology. The RFID technology is a technology which exchanges information through near-field radio communication using electromagnetic fields, radiowaves, and the like from an RF tag in which ID information is embedded. The RF tag may be configured with a circuit board in which a plurality of electronic elements are mounted or may be realized by an integrated circuit (IC). The user identifying unit 220 identifies a user, for example, by reading magnetic information included in an IC card owned by the user or magnetic information included in the user terminal using near-field radio communication. The reading function may be a contact type or a non-contact type. The user, for example, causes an IC card including magnetic information or the user terminal 300 to approach the user identifying unit 220 of the measurement device 200 or holds up the IC card or the user terminal for the user identifying unit 220, thereby causing the user identifying unit 220 to read the magnetic information.

In addition, the user identifying unit 220 may receive user identification information from the user terminal 300 using radio communication such as WiMAX, WiFi, Bluetooth, or the like. The user identifying unit 220 is not limited to such radio communication and, for example, may receive user identification information from the user terminal 300 using radio communication such as LTE, CDMA, or the like. In such a case, the user may transmit user identification information to the measurement device 200 by operating the user terminal 300. In addition, in a case in which the user terminal 300 is positioned in a predetermined area (for example, inside a toilet) or the like, the terminal 300 held by the user may be configured to automatically (without an operation of a user) transmit user identification information to the measurement device 200.

In this way, identification of a user can be automatically performed by holding up the user terminal 300 or the IC card for the user identifying unit 220, the network can be automatically identified, and furthermore, a specific organization (for example, a company, a hospital, a school, or the like) can be identified, and identification of the user can be performed in a simplified manner without the user operating and inputting information used for identifying the user or information used for identifying a specific organization every time when the user uses the toilet.

In addition, the user identifying unit 220 may be configured to include the measurement unit 221. For example, in the case of a western-type toilet, the measurement unit 221 measures the weight (weight in Kg) of a user accommodated by a toilet seat and stores information of the measured weight of each user (hereinafter, referred to as "weight information") in the memory unit 250. The user identifying unit 220 identifies a user on the basis of the weight information and generates user identification information. In addition, the user identifying unit 220 may identify a user through face authentication by including a face recognition sensor, through detection of a posture by including a posture detection sensor, through measurement of the pulse of the user by including a pulse measuring means, through measurement of blood pressure of the user by including a blood pressure measuring means, through measurement of a body fat percentage of the user by including a body fat percentage measuring means, or through measurement of a muscle mass of the user by including a muscle mass measuring means.

Such user identification information may be transmitted to the server 100 together with water temperature information, voltage information, user identification information, illuminance information, and imaging information forming a set therewith or may be transmitted at an identification timing. The user identifying unit 220 transmits the user identification information to the transmission unit 242 through the control unit 230 for transmitting the user identification information to the server 100. In this way, the identification of a user can be automatically performed during a part of an ordinary urination action, and the user can be identified in a simplified manner without inputting information used for identifying the user every time when the user uses the toilet.

<Data>

Here, in this embodiment, an example of the data configurations of various DBs stored in the memory unit 130 of the server 100 will be described with reference to FIG. 11 as one example. In addition, a storage destination of each of various DBs is not limited to the memory unit 130 and may be the memory unit 250 of the measurement device 200 or the memory unit 340 of the user terminal 300. In addition, it is apparent that the data configuration may be appropriately changed in accordance with the functional configuration of the server 100, the processing details, and the like.

First, a toilet information DB is a DB that stores information relating to a toilet and, for example, is configured to include information of a toilet model number, a water amount (a water level, a mass, a volume, and the like of reserved water), a water temperature (water temperature information of reserved water), presence/absence of a washing agent, an installation site (latitude/longitude information, an address, a building name, and the like), a use start time (a use start time of the toilet), and the like as one example. In addition, the toilet information DB may be configured to additionally include information relating to toilet environments (not illustrated in the drawing) such as information of the amount of a detergent and the like or composition information of a detergent and the like. The toilet information DB maintains records in units of toilets. In addition, information associated with a toilet model number (for example, shape information of a bowl of a toilet, water amount information of a toilet, and the like) may be stored in the DB or may be retrieved and acquired using a network system such as the Internet each time without being stored in the DB.

Next, a threshold DB is a DB that stores thresholds that are determination references for determining whether a measurement result is positive or negative, normal or abnormal, and the like and, for example, is configured to include information of measurement items, a threshold (absolute) for each measurement item (a reference value as an absolute index for each measurement item), a threshold (for each user) for each measurement item (a reference value as a personalized index for each user for each measurement item), and the like as an example.

Next, a measurement/inspection result DB is a DB that stores a measurement result and an inspection result for each user and, for example, is configured to include information of a user ID (user identification information), measurement items, measured values, inspection items, inspection results (an analysis result and a prediction result), a measurement date and time (year/month/date, hour/minute/second), an inspection date and time (year/month/date, hour/minute/second), and the like as an example.

Next, a dictionary data DB is a DB that stores dictionary data and, for example, is configured to include information of measured values, inspection results (an analysis result and a prediction result), and the like as one example. The dictionary data DB is used for identifying a characteristic vector generated from measured values as so-called teacher data in machine learning. In addition, the dictionary data stored in the dictionary data DB may be defined and stored in a settings file. By using the settings file, a reading speed and an update processing speed for dictionary data are higher than those of a case in which a DB is used.

Next, a user DB is a DB that stores information used for uniquely identifying a user and, for example, is configured to include information of a user ID (information of uniquely-assigned alphanumeric characters), a name of a user, sex, a height, a weight, mass information measured by the measurement device 200, toilet IDs of one or more toilets associated with the user, and the like as an example.

The data configurations of the various DBs have been described above.

Next, an example of the data configuration of association between measurement/analysis results and information of diseases and the like of the health monitoring system 500 will be described with reference to FIG. 12. FIG. 12 is a data concept diagram illustrating the association. For example, a color development state according to a color reaction of a film 90 reacted to a reagent or the like is measured by the imaging unit 280 using an immunochromatography method using an albumin composition in urine as input information, the concentration of albumin in the urine is analyzed on the basis of the color development state, and it is determined whether the concentration exceeds a corresponding threshold in a result of the analysis and the like as an example. A user predicts whether or not diabetes is positive or negative on the basis of a result of the determination.

<Operation>

FIG. 12 is a flowchart illustrating one example of a process executed by the health monitoring system 500.

The memory unit 130 stores shape information of a bowl of a toilet, water amount information of reserved water, water temperature information of the reserved water, environment information, and the like as an initial setting in advance or every time when measurement is performed (Step S11). The user identifying unit 220 identifies a user using an IC card, the user terminal 300, or the like (Step S12). In addition, after this step, the temperature measuring unit 212 may measure a water temperature of the reserved water once (not illustrated in the drawing). The illuminance sensor unit 290 measures illuminance of the surface of the film 90 (Step S13). In a case in which it is transmitted that measurement start has been manually input by an input means included in the control unit 230 from the user, the measurement unit 210 starts each measurement (Step S14). In addition, this step may be omitted in a case in which the electrode unit 211, the imaging unit 280, and the temperature measuring unit 212 automatically start measurement.

In a case in which measurement starts automatically or manually when the measured temperature reaches a predetermined threshold or the like, the temperature measuring unit 212 measures a temperature of the reserved water or urination-containing water and generates water temperature information (Step S15). In a case in which measurement starts automatically or manually when the measured electric potential difference reaches a predetermined threshold or the like, the electrode unit 211 measures an electric potential difference between the electrodes and generates voltage information (Step S16). In a case in which measurement starts automatically or manually, the transfer unit 260 and the storage unit 270 extrude a film 90 positioned at the bottom of the storage unit 270 by operating the extrusion part 273, and the transfer unit 260 clamps the film and immerses the film in the urination-containing water. The immersed film is imaged by the imaging unit 280, and imaging information is generated (Step S17).

The temperature measuring unit 212 automatically ends the measurement when the measured temperature reaches a predetermined threshold or the like, and the electrode unit 211 automatically ends the measurement when the measured electric potential difference reaches a predetermined threshold or the like (Step S18).

The interpretation unit 121 analyzes (calculates) the amount of urine by analyzing a fluid using a fluid model acquired by modeling the fluid flowing in the vicinity of the measurement unit 210 on the basis of the shape information of the toilet bowl, the water amount information, the water temperature information, and the like (Step S19). In the case of an analysis in which the measured value is acquired using the electrode method (the electrode method of Step S20), the correction unit 123 calculates a degree of dilution on the basis of the analyzed urine amount information and the water amount information and corrects the voltage information on the basis of the degree of dilution (Step S21). The analysis unit 122 analyzes urine compositions on the basis of the voltage information (after correction) (Step S22).

In the case of an analysis in which the measured value is acquired using the immunochromatography method (the immunochromatography method of Step S20), the correction unit 123 calculates a degree of dilution on the basis of the analyzed urine amount information and the water amount information and corrects the imaging information on the basis of the degree of dilution (Step S23). In addition, in this step, the correction unit 123 may correct the imaging information on the basis of the illuminance information in addition to the degree of dilution. The analysis unit 122 analyzes urine compositions on the basis of the imaging information (after correction) (Step S24). The analysis unit 122 generates a characteristic vector on the basis of a result of the analysis and identifies the generated characteristic vector using training data (dictionary data) (Step S25). The prediction unit 124 predicts a likelihood of having a disease of the user on the basis of the urination information (for example, analyzed urine compositions) of the analyzed urination (Step S26).

Advantages of the present invention will be described again. The health monitoring system 500 according to one aspect of the present invention analyzes compositions of urine by installing the measurement device 200 in a toilet or the like that has already been installed and immersing a film, which produces a color reaction with a composition to be detected, in the urination. At this time, a film is stored in the storage unit 270, and the transfer unit 260 takes the film out of the storage unit 270 and immerses the film in the urine at each time of measurement. Accordingly, urine compositions of a person to be measured can be measured by performing excretion for a toilet as usual, and accordingly, the urine compositions can be measured more simply and sanitarily than in a measurement performed by pouring urine over a device, whereby the usability can be improved.

In addition, the transfer unit 260 may change only the positional relation among the rods in opening/closing and rotation of the clamping unit 264 that clamps the film, whereby control can be simplified. In addition, depending on the driving, the clamping unit 264 may be open/closed or rotated while changing the position of the clamping unit 264. For this reason, a time required for the transferring of a film can be shortened.

In addition, the drive units driving the rods are arranged to be close to each other in the transfer unit 260, and the drive units are arranged at positions separate from the reserved water. For this reason, the size of the transfer unit 260 can be decreased, and the waterproof property of the drive units is improved, whereby the durability can be improved. In addition, the drive unit for clamping a film using the clamping unit 264 is not directly arranged in the clamping unit 264, and accordingly, the weight of the clamping unit 264 is decreased, the load applied to the driving is decreased, the drive unit is not close to the reserved water, and accordingly, there is also an advantage that an additional plan for the waterproof property does not need to be set up.

In addition, since the length of each rod in the transfer unit 260 can be adjusted at the time of design, there is a degree of freedom in the type of installable toilet.

In addition, a plurality of films are stacked in the storage unit 270 storing films, and the films are extruded only when urination is measured. Accordingly, urination can be measured in a simplified manner without a film being prepared every time measurement is performed. In addition, since the opening part 271 is closed by the lid part 272, a measurement result having high reliability can be acquired without degrading the durability of films.

In addition, a dehumidification mechanism 277 that includes at least one of a dehumidifier and a dehumidification module is further stored inside the storage unit 270. Accordingly, the durability and the quality of the films 90 can be maintained. In addition, the dehumidification mechanism 277 may be replaced when films 90 are newly supplemented after the films 90 are used up, or in a case in which the films 90 are used up, the entire storage unit 270 may be replaced. Accordingly, a validity period and the like of the dehumidification mechanism 277 do not need to be managed, and a health monitoring system enabling convenient use can be provided.

In addition, according to one embodiment of the present invention, urination is analyzed on the basis of fluid information relating to a fluid in reserved water into which urination of a user using a toilet has flown, and the accuracy of a result of the analysis using a film can be improved on the basis of urination information of the analyzed urination.

Although one aspect of the present invention has been described as above, it is apparent that the present invention is not limited thereto. For example, although an example of a service using a cloud service has been illustrated in the description presented above, the present invention can be used for a cloud doctor service using artificial intelligence (for example, machine learning using deep learning or the like) (for example, a service providing medical care in regard to a health state or a condition of a patient over a network) or a cloud mother service (for example, a service monitoring a health state or a condition of a child over a network).

In addition, a control unit may be disposed in the transfer unit 260 and may perform drive control and the like of the clamping unit 264 in the transfer unit 260. In such a case, in a case in which the immersion of a film in the urination is ended by the clamping unit 264, information indicating the end may be transmitted to the imaging unit 280 or the like.

In addition, a plurality of dehumidification mechanisms may be stored in the storage unit 270, and, for example, the dehumidifier may be disposed to surround the stacked films 90.

In addition, a specific device of the user terminal 300 is not limited to a smartphone as illustrated in the drawing and, for example, may be a mobile terminal, a tablet terminal, a personal computer, or any other electronic device. Although the user terminal 300, for example, includes a computer (for example, a desktop computer, a laptop computer, a tablet, or the like), a media computer platform (for example, a cable, a satellite set-top box, or a digital video recorder), a handheld computing device (for example, a personal digital assistant (PDA), an electronic mail client, or the like), a mobile phone (for example, a smartphone, a feature phone, or the like), a wearable terminal (a glass-type device, a watch-type device, or the like), a computer of a different type, or a communication platform, the present invention is not limited thereto. In addition, the health monitoring system 500 may use a cloud service (including both a public cloud service and a private cloud service), and the service may be provided by physically disposing a shared or dedicated server inside a target facility.

Each of the functional units of the server 100, the measurement device 200 and the user terminal 300 may be realized by a logic circuit (hardware) formed in an integrated circuit (IC) chip, a large scale integration (LSI), or the like or a dedicated circuit or may be realized by software using a central processing unit (CPU) and a memory. In addition, each of the functional units may be realized by one or a plurality of integrated circuits, and the functions of a plurality of functional units may be realized by one integrated circuit. The LSI may be also referred to as a VLSI, a super LSI, an ultra LSI or the like depending on a difference in the degree of integration. In addition, a "circuit" described here may include digital processing using a computer, in other words, may include a meaning of functional processing using software. Furthermore, the circuit may be realized by a re-configurable circuit (for example, a field programmable gate array (FPGA)).

In a case in which each of the functional units of the server 100, the measurement device 200, and the user terminal 300 is realized by software, each of the functional units of the server 100, the measurement device 200 or the user terminal 300 includes a CPU that executes commands of a display information generating program that is software realizing each function, the health monitoring program described above, a read only memory (ROM) or a memory device in which various kinds of data are recorded in a computer (or CPU) readable form (these will be referred to as "recoding media"), a random access memory (RAM) in which the health monitoring program described above is expanded, and the like. Then, as the computer (or the CPU) reads the health monitoring program described above from the recording media described above and executes the program, an object of the present invention is achieved. As the recording media described above, "a medium of a non-transitory type", for example, a tape, a disk, a card, a semiconductor memory, a programmable logic circuit, and the like may be used. In addition, the health monitoring program described above may be supplied to the computer through an arbitrary transmission medium (a communication network or a broadcast wave, or the like) that can transmit the health monitoring program. The present invention can be realized in the form of a data signal embedded in a carrier wave implemented by electronic transmission of the health monitoring program described above.

More specifically, a program according to an embodiment of the present invention realizes a transfer function, an imaging function, an analysis function, and a prediction function in the server 100 or the measurement device 200. The transfer function, the imaging function, the analysis function, and the prediction function may be respectively realized by the transfer unit 260, the imaging unit 280, the analysis unit 122, and the prediction unit 124 described above. Details thereof are as described above.

In addition, the health monitoring program described above, for example, may be implemented using a script language such as Action Script or JavaScript (registered trademark), an object-oriented programming language such as Objective-C, Java (registered trademark), a markup language such as HTML5, or the like.

EXPLANATION OF REFERENCES

100 Server
200 Measurement device
300 User terminal
400 Network
500 Health monitoring system
600 Toilet
110 Communication unit
111 Reception unit (acquisition unit)
112 Transmission unit
120 Control unit
121 Interpretation unit
122 Analysis unit
123 Correction unit
124 Prediction unit
125 Generation unit
130 Memory unit
210 Measurement unit
211 Electrode unit
212 Temperature measuring unit
220 User identifying unit
221 Measurement unit
230 Control unit
240 Communication unit
241 Reception unit
242 Transmission unit
250 Memory unit
260 Transfer unit
261 Upper rod (rack)
2611 Upper clamping member
2612 Upper bracket
2615 Upper pinion
2616 Upper drive unit
262 Lower rod (rack)
2621 Lower clamping member
2622 Lower bracket
2625 Lower pinion
2626 Lower drive unit
263a Moving rod (rack)
2635a First moving pinion
263b Moving rod (rack)
2635b Second moving pinion
2636 Moving drive unit
264 Clamping unit
265 Connection shaft
267 Housing unit
270 Storage unit
271 Opening part
272 Lid part
273 Extrusion part
275 Moving mechanism
276 Shaft
277 Dehumidification mechanism
280 Imaging unit
290 Illuminance sensor unit
310 Communication unit
311 Reception unit
320 Control unit
330 Display unit
340 Memory unit
312 Transmission unit
60 Top film
70 Reagent
80 Support body film
90 Film

What is claimed is:
1. A health monitoring system analyzing urination of a user using a toilet, the health monitoring system comprising:
   a storage unit that stores a film producing a color reaction for a composition to be detected;
   a transfer unit that immerses the film taken out of the storage unit in reserved water of the toilet into which the urination has flown;
   an imaging unit that generates imaging information by imaging the film after being immersed in the reserved water;

an analysis unit that analyzes urine compositions of the urination on the basis of the imaging information; and
a prediction unit that predicts a likelihood of having a disease on the basis of a result of the analysis using the analysis unit,
wherein the transfer unit includes:
a clamping unit that clamps the film in an opening/closing part of an upper clamping member and a lower clamping member of which one ends are connected through a connection shaft;
an upper drive unit that drives an upper rod to which the upper clamping member is connected in a longitudinal direction of the upper rod;
a lower drive unit that drives a lower rod to which the lower clamping member is connected in a longitudinal direction of the lower rod; and
a moving drive unit that drives a first moving rod connected to the upper clamping member through the connection shaft and a second moving rod connected to the lower clamping member through the connection shaft in longitudinal directions of the first moving rod and the second moving rod,
wherein the upper rod, the lower rod, the first moving rod, and the second moving rod are positioned approximately in parallel with each other in a longitudinal direction,
wherein the opening/closing part of the clamping unit is opened or closed by changing a relative position of at least one of the upper rod and the lower rod in the longitudinal direction with respect to the first moving rod and the second moving rod, and
wherein a position of the clamping unit is changed by moving the first moving rod, the second moving rod, the upper rod, and the lower rod in the longitudinal direction without changing relative positions of the upper rod and the lower rod with respect to the first moving rod and second moving rod.

2. The health monitoring system according to claim 1, wherein the transfer unit rotates the clamping unit using the connection shaft as its rotation shaft by changing the relative positions of the upper rod and the lower rod in the longitudinal direction with respect to the first moving rod and the second moving rod.

3. The health monitoring system according to claim 1, further comprising a housing unit that houses the moving drive unit, the upper drive unit, and the lower drive unit,
wherein, in a case in which the film clamped by the clamping unit is immersed into the reserved water, the housing unit is arranged at a position, which is separate from the clamping unit by a predetermined length, in the transfer unit.

4. The health monitoring system according to claim 1, wherein the transfer unit is arranged at a position at which the film can be taken out of the storage unit, and the film clamped by the clamping unit can be imaged by the imaging unit.

5. The health monitoring system according to claim 1, further comprising an illuminance sensor unit that measures illuminance of the toilet,
wherein the analysis unit corrects the imaging information on the basis of illuminance information relating to illumination of the toilet and analyzes urine compositions of the urination on the basis of the corrected imaging information.

6. The health monitoring system according to claim 1, wherein the storage unit stores the films to be stacked and includes:
an opening part;
an extrusion part that extrudes the film from the opening part;
a lid part that closes the opening part; and
a drive unit that drives the extrusion part and the lid part,
wherein, when the film is extruded by the extrusion part, the drive unit drives the lid part such that the opening part is open.

7. The health monitoring system according to claim 1,
wherein the storage unit stores the films to be stacked and includes:
an opening part; and
an extrusion part that extrudes the film from the opening part, and
wherein a dehumidification mechanism including at least one of a dehumidifier and a dehumidification module is further stored in the storage unit together with the films.

8. The health monitoring system according to claim 1, further comprising:
a measurement unit that measures fluid information relating to a fluid in reserved water into which urination of a user using the toilet has flown;
an acquisition unit that acquires shape information of a bowl of the toilet, water amount information of reserved water, and environment information relating to a surrounding environment of the measurement unit; and
an interpretation unit that analyzes the urination by analyzing a fluid model acquired by modeling a fluid on the basis of at least one of the fluid information measured by the measurement unit, the shape information, the water amount information, and the environment information,
wherein the analysis unit corrects the imaging information on the basis of urination information acquired as a result of an analysis using the interpretation unit and the fluid information and analyzes urine compositions of the urination on the basis of the corrected imaging information.

9. The health monitoring system according to claim 1, wherein the prediction unit generates a characteristic vector from the imaging information, identifies the generated characteristic vector using training data, and predicts a likelihood of having a disease on the basis of the identified characteristic vector.

10. A health monitoring method for analyzing urination of a user using a toilet, the health monitoring method comprising:
a storage step of storing a film producing a color reaction for a composition to be detected in a storage unit;
a transfer step of causing a transfer unit to immerse the film taken out of the storage unit in reserved water of the toilet into which the urination has flown using a transfer unit;
an imaging step of generating imaging information by imaging the film after being immersed in the reserved water;
an analysis step of analyzing urine compositions of the urination on the basis of the imaging information; and
a prediction step of predicting a likelihood of having a disease on the basis of a result of the analysis in the analysis step,
wherein the transfer unit includes:
a clamping unit that clamps the film in an opening/closing part of an upper clamping member and a lower clamping member of which one ends are connected through a connection shaft;

an upper drive unit that drives an upper rod to which the upper clamping member is connected in a longitudinal direction of the upper rod;

a lower drive unit that drives a lower rod to which the lower clamping member is connected in a longitudinal direction of the lower rod;

a moving drive unit that drives a first moving rod connected to the upper clamping member through the connection shaft and a second moving rod connected to the lower clamping member through the connection shaft in longitudinal directions of the first moving rod and the second moving rod; and a housing unit that houses the moving drive unit, the upper drive unit, and the lower drive unit, wherein the upper rod, the lower rod, the first moving rod, and the second moving rod are positioned approximately in parallel with each other in a longitudinal direction, and wherein, in the transfer step, the opening/closing part of the clamping unit is opened or closed by changing a relative position of at least one of the upper rod and the lower rod in the longitudinal direction with respect to the first moving rod and the second moving rod, and a position of the clamping unit is changed by moving the first moving rod, the second moving rod, the upper rod, and the lower rod in the longitudinal direction without changing relative positions of the upper rod and the lower rod with respect to the first moving rod and the second moving rod.

11. A non-transitory computer readable media comprising: a program controlling a health monitoring system analyzing urination of a user using a toilet, the program causing a computer to realize:

a transfer function of causing a transfer unit to take a film out of a storage unit storing films producing a color reaction for a composition to be detected and to immerse the film into reserved water of the toilet into which the urination has flown;

an imaging function of generating imaging information by imaging the film after being immersed in the reserved water;

an analysis function of analyzing urine compositions of the urination on the basis of the imaging information; and a prediction function of predicting a likelihood of having a disease on the basis of a result of the analysis using the analysis function, wherein the transfer unit includes:

a clamping unit that clamps the film in an opening/closing part of an upper clamping member and a lower clamping member of which one ends are connected through a connection shaft;

an upper drive unit that drives an upper rod to which an upper clamping member is connected in a longitudinal direction of the upper rod;

a lower drive unit that drives a lower rod to which a lower clamping member is connected in a longitudinal direction of the lower rod;

a moving drive unit that drives a first moving rod connected to the upper clamping member through a connection shaft and a second moving rod connected to the lower clamping member through the connection shaft in longitudinal directions of the first moving rod and the second moving rod; and a housing unit that houses the moving drive unit, the upper drive unit, and the lower drive unit, wherein the upper rod, the lower rod, the first moving rod, and the second moving rod are positioned approximately in parallel with each other in a longitudinal direction, and wherein the computer causes the transfer unit to:

open or close the opening/closing part of a clamping unit by changing a relative position of at least one of the upper rod and the lower rod in the longitudinal direction with respect to the first moving rod and the second moving rod; and change a position of the clamping unit by moving the first moving rod, the second moving rod, the upper rod, and the lower rod in the longitudinal direction without changing relative positions of the upper rod and the lower rod with respect to the first moving rod and the second moving rod.

* * * * *